(12) United States Patent
Papp et al.

(10) Patent No.: US 6,265,445 B1
(45) Date of Patent: Jul. 24, 2001

(54) ANTIARRHYTHMIC COMPOUNDS

(75) Inventors: Gyula Papp; András Varró, both of Szeged; Péter Mátyus, Budapest; Ildikó Varga, Budapest; Tivadar Rettegi, Budapest; Alice Druga, Budapest; Antal Simay, Budapest; Imre Moravcsik, Budapest; Pál Berzsenyi, Budapest, all of (HU); Daniella Barlocco; Giorgio Cignarella, both of Milan (IT); Márta Pátfalusi, Budapest (HU)

(73) Assignees: Gyogyszerkutato Intezet Kft; Szent-Gyorgyi Albert Orvostudomanyi Egyetem, both of Budapest (HU)

(*) Notice: Subject to any disclaimer, the term of this patent is extended or adjusted under 35 U.S.C. 154(b) by 0 days.

(21) Appl. No.: 09/555,602

(22) PCT Filed: Dec. 10, 1998

(86) PCT No.: PCT/HU98/00101

§ 371 Date: Sep. 27, 2000

§ 102(e) Date: Sep. 27, 2000

(87) PCT Pub. No.: WO99/29655

PCT Pub. Date: Jun. 17, 1999

(30) Foreign Application Priority Data

Dec. 11, 1997 (HU) .................................................. 9702411

(51) Int. Cl.[7] .......................... A61K 31/17; A61K 31/18; A61K 31/16; A61K 31/135

(52) U.S. Cl. .......................... 514/586; 514/605; 514/630; 514/654; 514/821; 564/27; 564/99; 564/220; 564/353; 564/354

(58) Field of Search ................................ 564/27, 99, 220, 564/353, 354; 514/586, 605, 630, 654, 821

(56) References Cited

U.S. PATENT DOCUMENTS

4,356,322 * 10/1982 Lehmann et al. .................... 564/185

* cited by examiner

*Primary Examiner*—Peter O'Sullivan
(74) *Attorney, Agent, or Firm*—Keil & Weinkauf (57) ABSTRACT

The present invention relates to novel, antiarrhythmically active phenoxyalkylamine derivatives possessing a double point of attack. More particularly, the present invention relates to new phenoxyalkylamine derivatives of the formula (1)

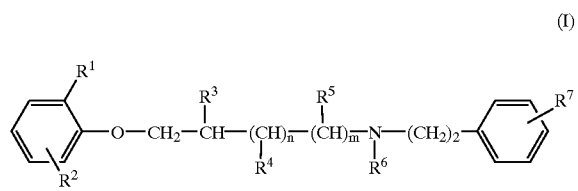

(I)

wherein
$R^1$ and $R^2$, independently from each other, mean hydrogen, halogen or $C_{1-4}$ alkyl group;
$R^3$, $R^4$ and $R^5$, independently from each other, stand for hydrogen or $C_{1-4}$ alkyl group;
$R^6$ represents hydrogen, $C_{1-4}$ alkyl or benzyl group;
$R^7$ means nitro group or amino group optionally monosubstituted by $C_{1-4}$ alkyl, benzoyl, $C_{1-4}$ alkylcarbonyl, $C_{1-4}$ alkylsulfonyl, $C_{1-4}$ alkylcarbamoyl or $C_{1-4}$ alkylthiocarbamoyl group;
both n and m are 0 or 1,
with the proviso that $R^2$ is different from hydrogen, when $R^1$ is hydrogen,
as well as stereoisomers or mixtures of stereoisomers thereof, acid addition salts thereof and hydrates, prodrugs and metabolites of all these compounds.

4 Claims, 2 Drawing Sheets

ANTIARRHYTHMIC COMPOUNDS

This application is a 371 of PCT/HU98/00101 filed Dec. 10, 1998.

The present invention relates to novel, antiarrhythmically active phenoxyalkylamine derivatives possessing a double point of attack. More particularly, the present invention relates to new phenoxyalkylamine derivatives of the formula (I)

and their salts as well as pharmaceutical compositions containing these compounds.

It is known that cardiac arrhythmias represent one of the most severe fields of cardiovascular disorders. Out of these, the most serious one is cardiac ventricular fibrillation, which is the most frequent immediate cause of the sudden cardiac death and leads to about 400,000 deceases in one year in the United States alone. Atrial fibrillation also accompanied by serious complications occurs at nearly one million persons. The most widely used method of treatment of arrhythmias is drug therapy. Nevertheless, the agents available at present cannot by far be considered to be the best solutions: their use may significantly be limited by their serious side effects. From this point of view, the negative results of two series of comprehensive clinical investigations [CAST I and CAST II. The CAST Investigators, N. Engl. J. Med. 321, 406 (1989) and ibidem 327, 227 (1992)] bringing to light that some so-called class IC antiarrhythmic agents with slow-recovery kinetics, which inhibit the maximal rate of repolarization of the action potential of heart, i.e. the sodium channel, deteriorated the chances of survival of patients recovering from myocardial infarction [an up-to-date classification of antiarrhythmics is presented e.g. by A. O. Grant., Jr. and N. C. Durham: Am. Heart J. 123, 1130, (1992)]. These unfavourable results can be brought into relation to the proarrhythmic (i.e. arrhythmia-provoking) effect and negative inotropic [i.e. cardiac performance (output)-weakening] effect of IC class antiarrhythmic agents. Later, it turned out that similarly, antiarrhythmic agents of class III, calling an increasing attention in the early 90's [which prolong the duration of action potential and therefore, the effective refractory period (abbreviated ERP)], are not free of dangerous side effects; and the clinical trials of d-sotalol (chemically d-N-[4-[1-hydroxy-2-(1-methylethylamino)ethyl]phenyl]methanesulfonamide hydrochloride) as a prototype of class III were even interrupted in the treatment group because of the increase in mortality ascribable to the proarrhythmic effect [see e.g. P. Mátyus, A. Varró, J. Gy. Papp et al.: Med. Res. Rev. 17, 427 (1997)].

There exist the dangers or limits, respectively, of the use of two additional antiarrhythmic drug classes (II and IV) as well as of two other subgroups (IA and IB) of the sodium channel blocking class I (especially in the case of classes IV and IA).

Even on the basis of those said above it is obvious that a high demand exists on a new type, safe but simultaneously suitably active antiarrhythmic agent. The aim of the invention is to develop an active agent and composition, respectively, meeting these requirements.

A number of phenoxyalkylamine derivatives are known in the literature. However, both their chemical structures and biological effects are different from the compounds of formula (I) of the present invention.

Hereinbelow, only the references describing the substances with structures most related to those according to the present invention are summarized.

The EP 245,997 relates to antiarrhythmically effective bis(arlkyl)amines and phenoxyalkylamine derivatives, from which some compounds exert a positive inotropic action, too. According to the authors, these compounds are selective antiarrhythmics of class III. The derivative of formula (VI)

containing methanesulfonamido group in 4-positions of both phenyl rings was found to be most active.

The published Japanese patent application No. 06,107,614 discloses compounds not falling within the scope of the present invention, which can be characterized by formula (I), wherein $R^1$, $R^2$ and $R^3$ mean hydrogen, both n and m are 0, or one of them is 1; $R^6$ means hydrogen, alkyl, formyl or alkylthiocarbamoyl group and $R^7$ stands for amino group substituted by p-chlorobenzenesulfonyl, 2,4,6-triisopropylbenzenesulfonyl, 8-quinolinesulfonyl, 1-naphthoyl or 2-pyridinecarbonyl group. According to the description these compounds are endowed of antiulcer effects.

In U.S. Pat. No. 4,044,150 4'-[1-hydroxy-2-[(1-phenoxyethyl)amino]ethyl]-methanesulfonanilide of formula (VII)

and the salts thereof are disclosed, which have a chemical structure standing near to a part of compounds of the present invention. According to the authors of this patent these substances are β-adrenerg receptor-blocking agents and as such they may be useful as antihypertensives.

Phenoxyalkylamine derivatives possessing chemical structures standing near to the compounds of the invention are known from GBP 2,088,873, wherein the phenoxy group can be mono- or disubstituted by hydrogen, halogen, hydroxyl or alkoxy group, while the phenyl group(s) on the other end of the alkylaminoalkyl chain can be di- or trisubstituted by a para-hydroxyl or amino group and/or meta-halogen(s) as well as trifluoromethyl, cyano or nitro group (s). According to the authors, these compounds act on the heart and circulation, more particularly they exert antihypertensive, antiarrhythmic and/or cardiotonic effects. However, the biological data given in the description confirm only the positive inotropic efficiency of the compounds.

Finally, it is mentioned as a point of interest that compounds analogous to substances of formula (I) of the invention, the phenoxy group of which is substituted by an acylamino group, and the phenyl group on the other end of the alkylaminoalkyl chain is substituted by a $C_{1-4}$alkyl or alkoxy group and/or halogen (which, consequently, contain a substitution inverse to the compounds of the invention), possess an antitumour effect (EP 494,623).

It has surprisingly been found during our investigations that the compounds of formula (I) possess a strong antiarrhythmic action and do not exhibit adverse side effects. In their mode of action, IB and III type effects are associated to result in a very favourable antiarrhythmic action of broader spectrum than those characterizing the individual components of action; this is a consequence of the combined mechanism. Simultaneously, it has been stated that the compounds of formula (I) are free from serious adverse effects, which are characteristic of the classes I and III.

These favourable pharmacological properties of the compounds of formula (I) are particularly surprising in view of the literature data. Namely, concerning the chemical structural requirements of antiarrhythmics of classes IB and III, there exists a standpoint that the antiarrhythmic action of class IB is characteristic of ortho-disubstituted phenoxyalkylamino (or isosteric) systems containing a short alkyl chain and an amino substituent with small steric demand (cf. e.g. tocainide, lidocaine); whereas compounds exerting a strong effect of class III are characterized by a structure containing two phenyl groups connected by a relatively long chain, wherein both of the phenyl groups have typically para-positioned, i.e. symmetrically situated, electron-attracting substituents [for the detailed analysis of structure-effect relations, see e.g.: P. Mátyus, A. Varró, J. Gy. Papp et al: Med. Res. Rev. 17, 427 (1997)].

Consequently, it is surprising even to one skilled in the art that compounds of formula (I) according to the invention, which have a structure fundamentally different from the typical representatives of antiarrhythmics of both classes IB and III, possess a significant antiarrhythmic effect associating the effects of both types IB and III while they are free from proarrhythmic or negative inotropic effects.

From the literature it is well known that compounds with a double point of attack are very important for the pharmaceutical chemistry [see e.g.: "The Practice of Medicinal Chemistry" pp. 261 to 293, Ed. C. G. Wermuth, Academic Press, London (1996)]. In the present case, the combination of the above-mentioned two antiarrhythmic mechanisms of action is even more advantageous than the usual one because it results in qualitatively new, extremely favourable properties; namely, due to the simultaneous presence of both components of action, the compounds of formula (I) do not exhibit either proarrhythmic or negative ionotropic effects. Otherwise, this combination of effects embodied in one and the same molecule is more preferred from the viewpoints of pharmakokinetics and drug safety, too, in comparison to the combination of both individual molecules.

When taken all together with the consideration that their toxicity is low, the compounds of formula (1) can be considered to be safe antiarrhythmic drug candidates of a new type with a broad spectrum of activities.

Thus, the invention relates to compounds of formula (I), (I)

wherein
$R^1$ and $R^2$, independently from each other, mean hydrogen, halogen or $C_{1-4}$ alkyl group;
$R^3$, $R^4$ and $R^5$, independently from each other, stand for hydrogen or $C_{1-4}$ alkyl group;
$R^6$ represents hydrogen, $C_{1-4}$ alkyl or benzyl group;
$R^7$ means nitro group or amino group optionally monosubstituted by $C_{1-4}$ alkyl, benzoyl, $C_{1-4}$ alkylcarbonyl, $C_{1-4}$ alkylsulfonyl, $C_{1-4}$ alkylcarbamoyl Of $C_{1-4}$ alkylthiocarbamoyl group;
both n and m are 0 or 1;
with the proviso that $R^2$ is different from hydrogen, when $R^1$ is hydrogen, as well as stereoisomers or mixtures of stereoisomers thereof, acid addition salts thereof and hydrates, prodrugs and metabolites of all these compounds.

In the compounds of the invention, alkyl groups may have a straight or branched carbon chain; halogen may mean bromine, chlorine or fluorine. According to those said above, in the formula (I) $R^1$ and $R^2$, independently from each other, may stand for methyl, ethyl, n-propyl, isopropyl or butyl group, furthermore fluorine, chlorine or bromine. In the case when one of $R^1$ and $R^2$ means hydrogen, the other should be different from hydrogen. Thus, the substituted phenoxy group in formula (I) may be e.g. 2,3-dimethylphenoxy, 2,4-dimethylphenoxy, 2,5-dimethylphenoxy, 2,6-dimethylphenoxy, 2,6-diethylphenoxy, 2-ethyl-6-methylphenoxy, 2-chloro-6-methylphenoxy, 2,6-dichlorophenoxy, 2-bromo-6-methylphenoxy, 2,6-dibromophenoxy, 2-bromo-4-chlorophenoxy, 2-methylphenoxy, 2-ethylphenoxy, 2-isopropylphenoxy, 2-chlorophenoxy, 2-bromophenoxy or 2-fluorophenoxy group.

$R^3$, $R^4$, $R^5$ and $R^6$, independently from each other, stand for hydrogen, methyl, ethyl, n-propyl, isopropyl or butyl group; additionally, $R^6$ may mean also benzyl group; $R^7$ may stand e.g. for nitro, amino, methylamino, ethylamino, propylamino, isopropylamino, butylamino, acetylamino, propionylamino, isopropionylamino, butanoylamino, benzoylamino, methanesulfonamido, ethanesulfonamido, n-propanesulfonamido, isopropylsulfonamido, butanesulfonamido, methylureido, ethylureido, n-propylurcido, isopropylureido, methylthioureido or ethylthioureido group.

An advantageous group of the compounds of formula (I) according to the invention is represented by substances, wherein $R^1$ means alkyl group, $R^2$–$R^7$ and n are as defined above and m is 0.

An other preferred group of compounds of the invention comprises compounds of formula (I), wherein $R^1$ and $R^2$ together stand for 2,6-dialkyl group, $R^3$ and/or $R^6$ mean(s) alkyl group, $R^7$ and n are as defined above and m is 0.

The compounds of formula (1) according to the invention can be prepared by using several methods known per se.

a) For the preparation of compounds of formula (I), wherein $R^1$ and $R^2$ mean alkyl group or halogen, or one of them means hydrogen, $R^3$, $R^4$, $R^5$, $R^6$, n and m are as defined above and $R^7$ stands for nitro group, e.g. a compound of formula (II), wherein $R^1$, $R^2$, $R^3$, $R^4$, $R^5$, $R^6$, n and m are as defined above, is reacted with 4-nitrophenethyl bromide. This reaction can be carried out under heating without any solvent or in various solvents, e.g. isopropanol, butanol or acetonitrile.

A part of the amino compounds of formula (II) employed as starting materials are known in the literature (e.g. BE 626,725; U.S. Pat. No. 3,659,019).

The compounds of formula (11) not described in the literature till now can be prepared by known methods. The preparation of novel compounds of formula (11) starting from compounds of formula (V)

is described in the Examples.

b) For the preparation of compounds of formula (1), wherein $R^1$ and $R^2$ stand for alkyl group or one of them is hydrogen, $R^3$, $R^4$, $R^5$, $R^6$, n and m are as defined above and $R^7$ stands for amino group, e.g. a compound of formula (I) wherein $R^1$, $R^2$, $R^3$, $R^4$, $R^5$, $R^6$, n and m are as defined above, and RF means nitro group, is reduced in a manner known per se. This reduction may be carried out by catalytical hydrogenation or catalytical transfer hydrogenation or in an other way known from the literature.

c) The preparation of compounds of formula (I), wherein $R^1$ and $R^2$ mean alkyl group or one of them stands for hydrogen, $R^3$, $R^4$, $R^5$, n and m are as defined above, $R^6$ means alkyl or benzyl group and $R^7$ represents alkylsulfonamido, benzamido, alkyl(thio)ureido or aliphatic alkylcarbonylamino (e.g. acetylamino) group, can be achieved e.g. by reacting compounds of formula (I), wherein $R^1$, $R^2$, $R^3$, $R^4$, $R^5$, $R^6$, n and m are as defined above, and $R^7$ means amino group, with a reagent suitable for introducing a sulfonyl group, or with acylating reagents in various solvents.

According to a preferred embodiment of the above process c) compounds, wherein $R^7$ means alkylsulfonamido, benzamido or alkylcarbonylamino group, are reacted in the presence of an acid-binding agent (e.g. triethylamine). This reaction is performed at room temperature or, if necessary, the reaction mixture is cooled or heated.

According to an other preferable embodiment of the above process c) compounds, wherein $R^7$ means an alkyl (thio)ureido group, are reacted in dioxane without any acid-binding agent at room temperature or under heating.

d) For the preparation of compounds of formula (1), wherein $R^1$ and $R^2$ mean alkyl group or one of them is hydrogen, $R^3$, $R^4$, $R^5$, n and m are as defined above, $R^6$ stands for alkyl group and $R^7$ represents alkylamino group, e.g. a compound of formula (I), wherein $R^1$, $R^2$, $R^3$, $R^4$, $R^5$, $R^6$, n and m are as defined above, and $R^7$ means alkylcarbonylamino group, can be reduced in a way known per se.

According to a preferred embodiment of process d) this reduction is carried out by using lithium aluminum hydride at the boiling point of tetrahydrofuran.

e) For the preparation of compounds of formula (1), wherein $R^1$ and $R^2$ mean alkyl group, halogen or one of them is hydrogen, $R^3$, $R^4$, $R^5$, n and m are as defined above, $R^6$ stands for alkyl group, hydrogen or benzyl group, and $R^7$ represents methanesulfonamido group, e.g. a compound of formula (III), wherein $R^1$, $R^2$, $R^3$, $R^4$, $R^5$, $R^6$, $R^7$, n and m are as defined above, is reduced in a manner known per se.

According to an advantageous embodiment of process e) this reduction is established by using lithium aluminium hydride in tetrahydrofuran at the boiling point.

The compounds of formula (III) used in process e) can be prepared e.g. by reacting amines of formula (II) with (methanesulfonamido)phenylacetic acid.

According to a preferable embodiment of the above process used for the preparation of compounds of formula (III), the reaction is carried out in N,N-dimethylformamide, in the presence of 4-methylmorpholine, isobutyl chloroformate and triethylamine at a temperature of –10° C. and later 0° C.; or the reaction is performed in tetrahydrofuran in the presence of dicyclohexylcarbodiimide.

f) For preparing compounds of formula (I), wherein $R^1$ and $R^2$ mean alkyl group, halogen or one of them is hydrogen, $R^3$, $R^4$, $R^5$, $R^6$, n and m are as defined above and RF stands for a methanesulfonamido group, e.g. a compound of formula (II), wherein $R^1$, $R^2$, $R^3$, $R^4$, $R^5$, $R^6$, n and m are as defined above, is reacted with N-[4-(2-bromoethyl)-phenyl]methanesulfonamide.

According to a preferred embodiment of process f) this reaction can be carried out without any solvent under heating.

The salts of compounds of formula (I) of the invention are directly formed in the reaction of their preparation or, when the compounds of formula (I) are separated in their base form, the salts can be prepared from the base obtained by dissolving the base in a suitable solvent, such as methanol, ethanol, isopropanol, ethyl ether, ethyl acetate or in a mixture thereof; and then adding to the solution the appropriate acid dissolved in a suitable solvent. The salts can be separated directly by filtration or optionally, by precipitation after addition of a suitable solvent; or by complete or partial evaporation of the solvent.

Frequently, the salts of compounds of formula (I) according to the invention contain the acid component in a non-stoichiometric ratio and/or they frequently crystallize in a hydrate form. The invention relates to these crystal forms, too.

The compounds of formula (I) according to the invention may optionally contain also asymmetrical carbon atoms and therefore, they may occur in optically active and racemic modifications. Optically pure compounds can be prepared from optically pure precursors as starting materials; or the racemic end product can be resolved. In the latter case, the optical isomers can be separated e.g. by treating the racemic compound e.g. in methanol, ethanol, ethyl acetate, acetone or an other solvent with an optically active acid, e.g. with a 0.5 to 2.0 molar amount [calculated for the compound of formula (I)] of e.g. D-tartaric acid, O,O-dibenzoyl-1-tartaric acid, O,O-dibenzoyl-D-tartaric acid-N,N-dimethylmonoamide, L-thiazolidine-4-carboxylic acid or an other usual, optically active acid to obtain the diastereomer salt of one optical isomer in an immediately pure state or optionally after several recrystallizations (depending upon the acid used); and the other isomer is obtained by processing of the mother liquors in the base form or in the form of a salt thereof (which depends on the amount of the acid used), which is further purified, when necessary.

Then, the optically active bases can be liberated from their salts thus obtained and separated, if desired, to prepare from the base obtained an acid addition salt with a therapeutically acceptable acid.

As mentioned above, the compounds of formula (I) according to the invention possess valuable antiarrhythmic effects.

In the following, the pharmacological results are discussed, which prove the IB- and III-class cardiac electrophysiological effect of compounds of formula (I) without a negative inotropic action and arrhythmia-inducing, i.e. proarrhythmic, effect, respectively, which are characteristic of classes IB and III. Finally, the in vivo antiarrhythmic action of the compounds of formula (I) will be shown in three arrhythmia models.

Extracellular Electrophysiological Measurements

The method used is essentially in agreement with the method of Varró et al. [Arch. Int. Pharmacodyn. Ther. 292, 157–165 (1989)].

Right ventricular trabecules were prepared from the heart of mongrel dogs (weighing 5 to 10 kg each). The surviving heart pieces were placed into an organ bath (37° C.) containing modified Tyrode's nutrient medium and excited by point stimulation with a basal frequency of 1 Hz. Extracellular bipolar platinum electrodes were placed on the surface of the preparations, by means of which the propagation of the superficial potentials were registered; thus, the determination of the time of impulse conduction or the rate of impulse conduction, respectively, and the effective refractory period (ERP) became possible. During our experiments, the frequency of stimulation was temporarily varied from 0.5 Hz up to 3 Hz. The tested compounds were directly added to the organ bath after dilution of the stock solution according to the desired final concentration. The effects of the compounds were observed after waiting for an incubation period of 30 to 40 minutes.

The results of the extracellular in vitro cardiac electrophysiological measurements are shown in Table 1.

TABLE 1

Effects of compounds investigated on the impulse conduction and effective refractory period (ERP) on isolated right ventricular trabecule of dog heart

| Example (10 $\mu$M) | N | Prolongation (%) of impulse conduction time | | Prolongation (%) of ERP | |
|---|---|---|---|---|---|
| | | 1 Hz | 3 Hz | 1 Hz | 3 Hz |
| 9 (2 $\mu$M) | 12 | +38.0 ± 3.5 | +51.3 ± 4.9 | +31.8 ± 2.5 | +39.4 ± 5.0 |
| 15 | 16 | +42.0 ± 7.5 | +73.8 ± 8.3 | +22.8 ± 1.3 | +31.3 ± 1.6 |
| 15 (2 $\mu$M) | 8 | +11.1 ± 2.2 | +13.4 ± 2.8 | +11.6 ± 1.2 | +13.6 ± 2.9 |
| 16 | 12 | +26.9 ± 3.1 | +39.7 ± 3.1 | +10.7 ± 0.7 | +14.3 ± 1.7 |
| 17 | 12 | +32.5 ± 6.0 | +35.1 ± 5.9 | +12.1 ± 0.9 | +17.1 ± 2.1 |
| 18 | 12 | +18.5 ± 2.4 | +21.7 ± 4.0 | +9.9 ± 0.8 | +14.0 ± 1.3 |
| 20 | 12 | +20.3 ± 2.7 | +24.5 ± 3.5 | +8.4 ± 0.3 | +12.6 ± 0.6 |
| 22 | 12 | +22.6 ± 4.1 | +28.3 ± 5.3 | +12.3 ± 1.3 | +18.1 ± 1.8 |
| 23 | 12 | +25.0 ± 3.9 | +25.0 ± 4.2 | +10.8 ± 1.1 | +14.9 ± 1.4 |
| 24 | 12 | +69.0 ± 11.9 | +82.9 ± 11.0 | +13.8 ± 1.7 | +18.4 ± 1.2 |
| 25 | 12 | +18.8 ± 2.0 | +18.8 ± 3.1 | +11.7 ± 1.2 | +17.0 ± 1.3 |
| Mexiletine (10 $\mu$M) | 6 | +3.9 ± 1.8 | +18.8 ± 2.5 | −1.9 ± 1.7 | +8.9 ± 5.4 |
| d-Sotalol (30 $\mu$M) | 8 | −4.5 ± 5.1 | −3.7 ± 4.7 | +12.4 ± 2.3 | +7.1 ± 2.7 |

N: Total number of animals in the group.

From the compounds investigated, the compounds of Examples 9, 15, 16, 17 and 24 significantly prolonged the time of impulse conduction in a frequency-dependent manner, i.e. they diminished the rate of impulse conduction together with the simultaneous prolongation of the effective refractory period (ERP). Mexiletine (chemically 2-(2,6-dimethylphenoxy)-1-methylethylamine hydrochloride) used as reference substance exerted an effect mainly on impulse conduction whereas d-sotalol showed a considerable effect only on the ERP.

Intracellular Microelectrode Techniques

The method used is essentially in agreement with the method of Papp et al. [J. Cardiovascular Pharmacol. Ther. 1, 287–296 (1996)].

Right ventricular papillary muscle and Purkinje's fibres were prepared from the hearts of mongrel dogs (weighing 5 to 10 kg each). The preparations were placed into an organ bath (37° C.) containing modified Tyrode's nutrient medium. The preparations were excited by a basal frequency of 1 Hz. During the experiments, the frequency of stimulation was varied under broad limits by a computer-guided stimulator. The intracellular action potentials were registered by using glass capillary microelectrodes filled with 3 N potassium chloride solution (standard intracellular microelectrode techniques). The resting potential (RP), the amplitude of the action potential (APA) as well as the duration of the action potential (APD) were measured by using an IBM 386 compatible computer by means of an own-developed software. The compounds under test were directly added into the organ bath after dilution of the stock solutions according to the final concentrations desired. The effects of the compounds were observed after an incubation time of 30 to 40 minutes.

The results of intracellular cardiac electrophysiological measurements on the papillary muscle are shown in Table 2. From the compounds tested, the compounds of Examples 9, 14, 15, 16, 17, 22, 26 and 27 induced a mexiletine-like inhibition of $V_{max}$, which can be characterized by a relatively significant degree of rapid recovery kinetics together with the simultaneous prolongation of duration of the action potential (APD) (dofetilide-like effect; chemically, dofetilide is N-[4-[2-[N-methyl-N-[2-(4-methanesulfonamidophenoxy)ethyl]-amino]ethyl]phenyl] methanesulfonamide). No essential difference could be observed between the effects of the compound of Example 15 and its enantiomers (Examples 16 and 17) in this experiment.

TABLE 3

Effect of the compound of Example 15 on the action potential on Purkinje's fibres isolated from dog heart

| Parameter | N | Control | Example 15 2 μM |
|---|---|---|---|
| MDP (mV) | 3 | −82.0 + 2.1 | −81.7 ± 2.4 |
| APA (mV) | 3 | 111.3 ± 3.8 | 112.7 ± 3.9 |
| $APD_{50}$ (ms) | 3 | 261.7 ± 36.2 | 180.7 ± 14.8 |
| $APD_{90}$ (ms) | 3 | 468.0 ± 81.1 | 400.0 ± 47.4 |
| $V_{max}$ (V/s) | 3 | 397.3 ± 25.4 | 392.3 ± 23.7 |

MDP: maximal diastolic potential;
APA: amplitude of the action potential;
$APD_{50}$: time of 50% repolarization;
$APD_{90}$: time of 90% repolarization;
$V_{max}$: maximum rate of depolarization;
N: total number of animals in the group.

TABLE 2

Effects of the compounds under test on the action potential parameters of the right ventricular papillary muscle of dogs

| Example (5 μM) | RP mV | APA mV | $APD_{50}$ ms | $APD_{90}$ ms | $V_{max}$ V/s | Recovery $T_{recovery}$ ms | Ampl V/s | Plateau V/s | Ampl/Plateau V/s |
|---|---|---|---|---|---|---|---|---|---|
| Control | −91 | 111 | 254 | 305 | 215 | | | | |
| 9 (1 μM) | −91 | 110 | 285 | 342 | 200 | 307.4 (Gy) | 132.4 | 216.5 | 0.61 |
| Control | −88 | 113 | 214 | 247 | 244 | | | | |
| 14 | −90 | 114 | 214 | 257 | 232 | 111.4 (Gy) | 58.7 | 231.8 | 0.25 |
| Control | −84 | 107 | 195 | 234 | 206 | <30 | — | — | — |
| 15 | −85 | 106 | 210 | 261 | 203 | 270.1 (Gy) | 83.6 | 245.5 | 0.35 |
| Control | −85 | 103 | 193 | 228 | 209 | <30 | — | — | — |
| 16 | −86 | 105 | 195 | 244 | 199 | 249.5 (Gy) | 75.8 | 196.4 | 0.39 |
| Control | −87 | 107 | 194 | 230 | 193 | | | | |
| 17 | −87 | 106 | 203 | 249 | 169 | 390.4 (Gy) | 85.2 | 173.7 | 0.52 |
| Control | −84 | 102 | 211 | 250 | 183 | | | | |
| 22 | −80 | 100 | 215 | 260 | 159 | 337.8 (Gy) | 136.3 | 232.8 | 0.58 |
| Control | −83 | 110 | 191 | 225 | 207 | | | | |
| 26 | −80 | 105 | 200 | 250 | 195 | 199 (Gy) | 120.9 | 195.9 | 0.62 |
| Control | −72 | 90 | 196 | 232 | 146 | | | | |
| 27 | −71 | 88 | 210 | 250 | 117 | 161.8 (Gy) | 78 | 147.9 | 0.53 |
| Control | −92 | 115 | 236 | 264 | 216 | | | | |
| Mexiletine (10 μM) | −92 | 115 | 244 | 270 | 193 | 214.1 (Gy) | 84.0 | 186.5 | 0.45 |
| Control | −79 | 100 | 186 | 214 | 227 | | | | |
| Dofetilide (1 μM) | −76 | 96 | 218 | 252 | 212 | — | — | — | — |

RP: resting potential; APA: amplitude of the action potential; APD: duration of the action potential; $APD_{50}$: time of 50% repolarization; $APD_{90}$: time of 90% repolarization; $V_{max}$: maximum rate of depolarization; $T_{recovery}$: recovery time constant of $V_{max}$; Gy: kinetics of rapid restoration.

The effects of the tested compounds according to the invention on the action potential of Purkinje's fibres isolated from dog heart are summarized on the compound of Example 15 in Tables 3 and 4.

The compound of Example 15 (5 μM) prolonged APD in the ventricular muscle of the dog and simultaneously abbreviated APD on Purkinje's fibres of the dog in concentrations of 2 μM and 5 μM. This result is extremely important since it can be expected that the compound would not increase but rather decrease the inhomogeneity of ventricular repolarization (which is an important proarrhythmic factor).

TABLE 4

Effect of the compound of Example 15 (5 μM) on the action potential on the ventricular muscle and Purkinje fibres of dog heart at stimulation frequency of 1 Hz

| | Ventricular muscle | | Purkinje's fibre | |
|---|---|---|---|---|
| | Control | Example 15 | Control | Example 15 |
| Parameter | N = 6 | | N = 6 | |
| RP (mV) | −84.3 ± 1.4 | −84.5 ± 1.3 | −87.7 ± 1.3 | −86.0 ± 2.0 |
| APA (mV) | 106.8 ± 2.2 | 106.3 ± 2.0 | 118.7 ± 0.9 | 111.0 ± 2.4* |
| $APD_{50}$ (ms) | 195.0 ± 6.7 | 209.5 ± 7.1* | 313.5 ± 26.0 | 121.3 ± 13.8* |
| $APD_{90}$ (mS) | 234.2 ± 9.4 | 260.5 ± 6.5* | 461.5 ± 26.5 | 279.0 ± 11.2* |
| $V_{max}$ (V/s) | 206.0 ± 3.5 | 203.0 ± 11.4 | 577.5 ± 35.9 | 439.3 ± 34.4* |
| $V_{max}$ | | | | |

| | | | | |
|---|---|---|---|---|
| time of recovery T (ms) $V_{max}$ | <30 ms | 270.1 ± 14.4 | — | — |
| time of recovery amplitude (V/s) $V_{max}$ | — | 83.6 ± 13.5 (35 ± 5%) | — | — |
| time of recovery plateau phase (V/s) | — | 245.5 ± 28.0 | — | — |

*p < 0.05
N: total number of animals in the group.

Figure 1:
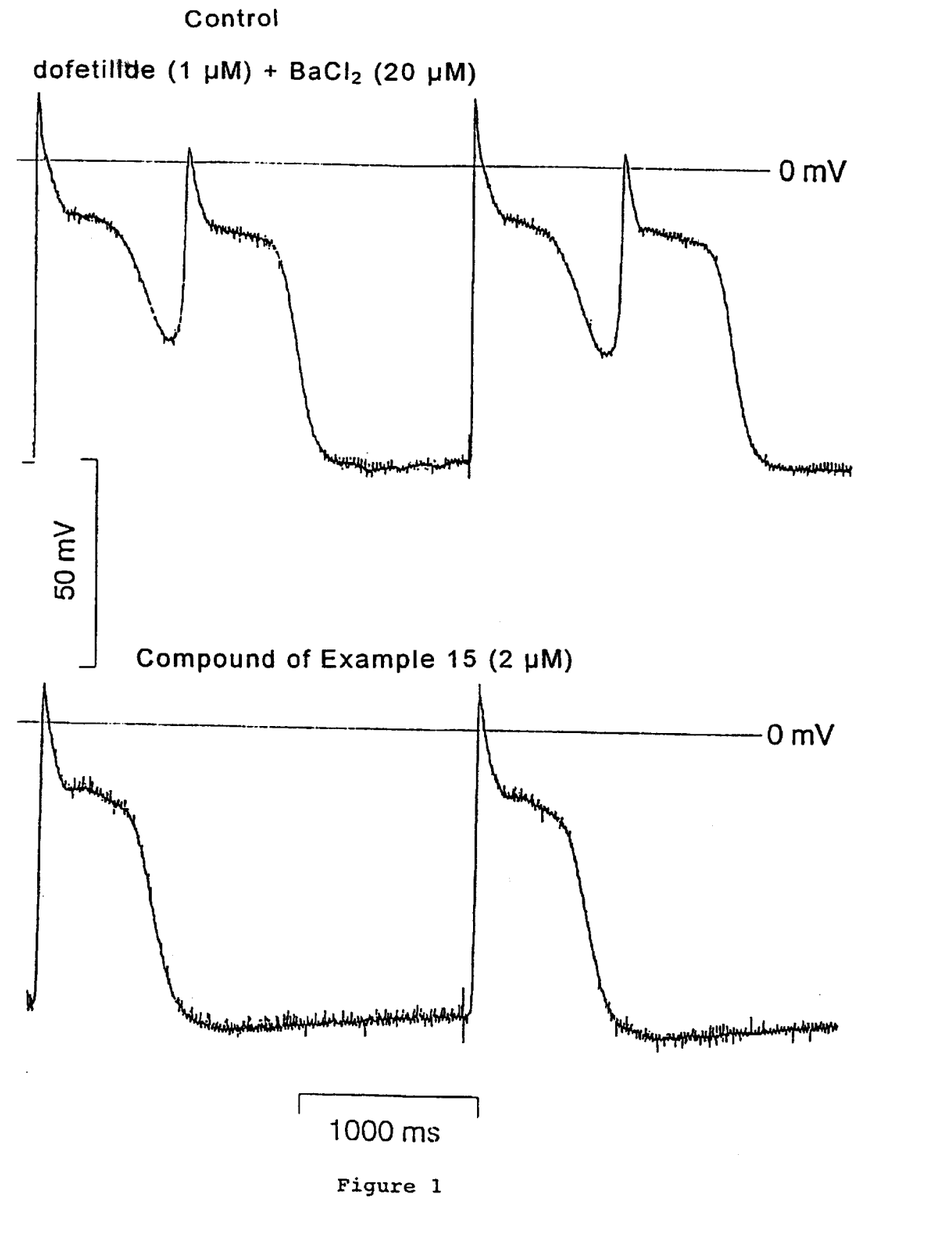
FIG. 1 graphically shows the effect on early after-depolarization of the compound of Example 15.

Investigation of the Effect on Early After-Depolarization (FIG. 1)

An early after-depolarization (EAD) was induced on dog Purkinje's fibres by the simultaneous use of 1 μM dofetilide and 20 μM BaCl$_2$. These EAD-s were abolished by the addition of the compound (2 μM) of Example 15. The result of these experiments indicates that, in contrast with d-sotalol, it can be expected that the compound of Example 15 would not induce a "torsade de pointes" type tachycardia, i.e. a proarrhythmic complication connected with prolongation of the repolarization.

Measurement of the Contractile Force In Vitro

The method used is essentially in agreement with the method of Virág et al. [Gen. Pharmac. 27, pp. 551–556 (1996)].

Papillary muscles of hearts of rabbits (weighing 2 to 3 kg each) were prepared and placed into an organ bath (37° C.) containing modified Tyrode's nutrient medium. The preparations were stimulated by point-stimulation with a basal frequency of 1 Hz. The contractile force was measured by using an auxotonic method. The compounds under test were directly added into the organ bath after dilution of the stock solution according to the final concentration desired. The effects of compounds were observed after an incubation period of 30 to 45 minutes.

Figure 2:
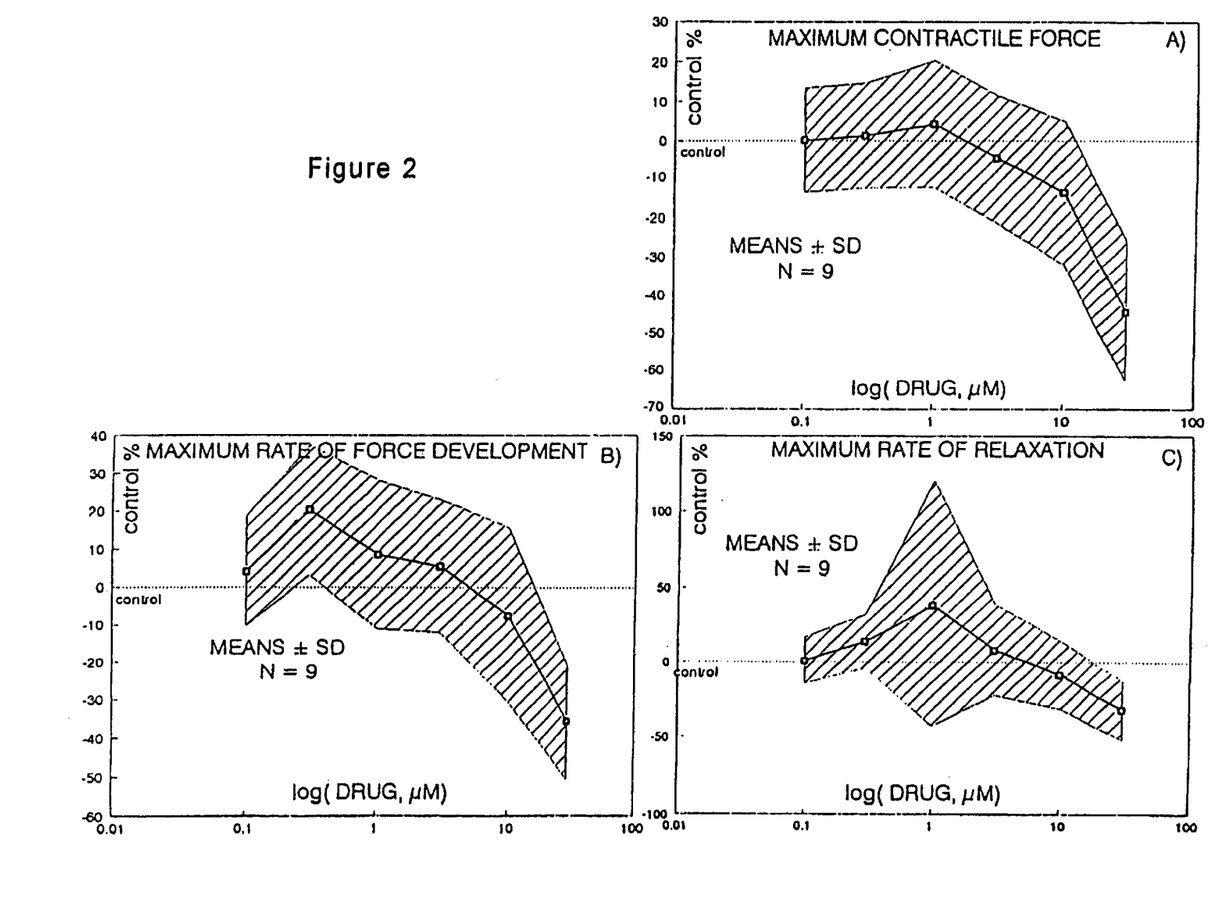
FIG. 2 shows the direct cardiac effects of the compound of Example 15.

Using this method used information can be obtained concerning the direct cardiac effects of the compounds investigated. The effect of the compound of Example 15 on the contractile force is illustrated on the right ventricular papillary muscle at a frequency of 1 Hz in FIG. 2. The results showed that the expected therapeutic concentration of Example 15 did not induce any negative inotropic action since the contractile force of papillary muscle was not decreased by using a concentration lower than 30 μM.

Acute Toxicity

Determination of the LD$_{50}$ Value on Mice

Animal: male CDI mice (starved) weighing 20 to 22 g each at the time of treatment.

Observation period: 2 weeks.

Vehicle: 1 to 2% of Tween-80 in distilled water or in physiological saline, respectively.

Treatment volume 0.1 ml/10 g of body-weight.

The results are shown in Table 5.

TABLE 5

Acute toxicity data of the tested compound of Example 15 and mexiletine as reference substance

| Compound | Route of administration | Concentration (mg/kg) | Mortality | LD$_{50}$ (mg/kg) (cause of death) |
|---|---|---|---|---|
| Example 15 | i.p. | 150 | 1/10 | 170.4 (154.3–188.2) (respiratory paralysis) |
| | | 175 | 7/10 | |
| | | 200 | 9/10 | |
| | p.o. | 500 | 0/5 | 550–650 (respiratory paralysis) |
| | | 600 | 2/5 | |
| | | 700 | 5/5 | |
| Mexiletine | i.p. | | | 130 (respiratory paralysis) |
| | p.o. | | | 300 (respiratory paralysis) |

Investigation of Occlusion and Reperfusion Induced Arrhythmias Following Acute Coronary Artery Ligation in Anaesthetized Rabbits The method used is essentially in agreement with the method of Thiemermann et al. [Br. J. Pharmacol. 97, pp. 401–408 (1989)].

A loose surgical thread loop was placed round the left circumflex coronary artery of the heart following thoracotomy in pentobarbital (30 mg/kg i.v.) anaesthetized male rabbits (weighing 2 to 3 kg); both ends of the thread loop were led out from the chest through an elastic tube. Standard electrocardiogram was registered by using needle electrodes under the skin. The blood pressure of animals was continuously measured by using a catheter placed into the common carotid artery. After stabilization of the blood pressure and heart frequency, the loose loop was tightened to establish a regional myocardial ischaemia. After 10 minutes of ischaemia, the ligature was released and a reperfusion for 10 minutes was established. The survival, the incidence of arrhythmias, the time of onset of arrhythmia and the length of episodes were registered. The animals received physiological saline solution (control) intravenously (2 ml/kg) or 0.03 mg/kg of the compound of Example 15 or a 3 mg/kg dose of d-sotalol at 5 minutes before the occlusion.

By using this method, it can be stated whether the compound under test would be effective for the protection from arrhythmias following coronary artery ligation. The experiments carried out indicated (see Tables 6 and 7) that the compound of Example 15 administered in a dose of 0.03 mg/kg possesses a strong antiarrhythmic effect on rabbits against reperfusion arrhythmias induced by ligation.

TABLE 6

Investigation into occlusion and reperfusion arrhythmias following acute coronary vessel compression in anaesthetized rabbits

| Occlusion | Free | VF | VT | Salvo | Bigeminy | VEB | S + B + VEB | Brady | Death |
|---|---|---|---|---|---|---|---|---|---|
| Control | 2/11 (18%) | 5/11 (45%) | 1/11 (9%) | 3/11 (27%) | 6/11 (55%) | 8/11 (73%) | 9/11 (82%) | 0/11 (0%) | 5/11 (45%) |
| d-Sotalol* | 5/11 (45%) | 1/11 (9%) | 0/11 (0%) | 2/11 (18%) | 6/11 (55%) | 3/11 (27%) | 6/11 (55%) | 1/11 (9%) | 0/11 (0%) |
| Example 15** | 2/11 (18%) | 3/11 (27%) | 2/11 (18%) | 1/11 (9%) | 4/11 (36%) | 9/11 (82%) | 9/11 (82%) | 0/11 (0%) | 0/11 (0%) |

TABLE 7

| Reperfusion | Free | VF | VT | Salvo | Bigeminy | VEB | S + B + VEB | Brady | Death |
|---|---|---|---|---|---|---|---|---|---|
| Control | 0/6 (0%) | 4/6 (67%) | 4/6 (67%) | 0/6 (0%) | 0/6 (0%) | 3/6 (50%) | 3/6 (50%) | 0/6 (0%) | 3/6 (50%) |
| d-Sotalol* | 3/11 (27%) | 2/11 (18%) | 4/11 (36%) | 7/11 (64%) | 6/11 (55%) | 8/11 (73%) | 8/11 (73%) | 0/11 (0%) | 2/11 (18%) |
| Example 15** | 3/11 (27%) | 3/11 (27%) | 4/11 (36%) | 1/11 (9%) | 2/11 (18%) | 5/11 (45%) | 6/11 (55%) | 1/11 (9%) | 3/11 (27%) |

*3.0 mg/kg; **0.03 mg/kg; Free: no arrhythmia occurred; VT: ventricular tachycardia; VF: ventricular fibrillation; VEB: sporadic ventricular extrasystole; S: salvo; B: bigeminy; Brady: bradycardia.

Investigation of Occlusion and Reperfusion Arrhythmias Following Acute Coronary Ligation in Anaesthetized Dogs The method used is essentially in agreement with the method of Vegh et al. [Basic Res. Cardiol. 82, 159–171 (1987)].

Mongrel dogs of both sexes weighing 10 to 20 kg each were anaesthetized by a mixture of chloralose (60 mg/kg) and urethane (200 mg/kg) and the animals were maintained on artificial respiration. After opening the chest, the ramus descendens anterior (LAD) branch of the left coronary artery of heart was prepared from the first main collateral branch and a loose loop from surgical thread was placed around it. During our experiments, the blood pressure of the animal was measured by using a cannule introduced to the left femoral artery and even the standard ECG parameters by using needle electrodes were continuously registered. The arrhythmias were induced by the occlusion for 25 minutes of a loop placed round the LAD. The survival after lethal arrhythmias and frequency of the arrhythmias were registered. The 28 dogs used in the experiments were divided into three groups. The compound of Example 15 was administered in a dose of 1 mg/kg to 8 animals; d-sotalol was given in a dose of 3 mg/kg to 10 animals by a single intravenous injection 10 minutes before compression of the coronary vessel. The control dogs (10 animals) received 5 ml of physiological saline solution in the same manner as the treated animals.

By using this method it can be stated whether the substance investigated would be effective for protection against arrhythmias following the ligation of the coronary artery. The experiments carried out indicated (Table 8) that a dose of 1 mg/kg of the substance of Example 15 protected from the arrhythmogenic effects of ligation and reperfusion of the coronary artery to a higher degree than a dose of 3 mg/kg of d-sotalol, an observation proving the significant antiarrhythmic effectivity of this compound.

TABLE 8

Investigation of occlusion and reperfusion arrhythmias following acute compression in anaesthetized dogs

| Compound | N | Occlusion | | | Reperfusion | Complete survival |
|---|---|---|---|---|---|---|
| | | ES | VT | VF | VF | |
| Control | 10 | 327 ± 22 | 10/10 100% | 6/10 60% | 4/4 100% | 0/7 0% |
| d-Sotalol (3 mg/kg) | 10 | 128 ± 14 | 5/10 50% | 3/10 30% | 2/7 29% | 5/10 50% |
| Example 15 (1 mg/kg) | 8 | 36.6 ± 84.1 | 1/8 12.5% | 1/8 12.5% | 0/7 0% | 7/8 87.5% |

ES: extrasystole; VT: ventricular tachycardia; VF: ventricular fibrillation; N: total number of animals in the group.

Occlusion Arrhythmia Following Acute Coronary Artery Ligation in Conscious Rats

The method used is essentially in agreement with the method of Lepran et al. [J. Pharmacol. Methods 9, pp. 219–230 (1983)].

During a previous operation, male rats weighing 340 to 360 g each were fitted with a loose surgical thread loop around the left descending coronary vessel, at about 2 mm from its origin. The ends of the loop thread were led out from the chest under the skin, then the surgical wound was closed. After complete recovery from this previous operation (7 to 8 days) acute myocardial ischaemia was induced by contracting the loose ligation in the conscious, freely moving animals. ECG was continuously registered by using bipolar chest electrodes before the ligation of the coronary artery and during the first 15 minutes of ischaemia. The ratio of survivals was determined and the developed arrhythmias were evaluated according to the Lambeth Convention [Walker et al.: Cardiovasc. Res. 22, 447–455 (1988)]. For evaluation of the arrhythmic episodes a score system was also employed by considering the severity of episodes on the basis of a score system from 0 to 6. Both d-sotalol and the substance of Example 15, respectively, were suspended in 1% methylcellulose and administered orally through a gastric sound at 1 hour before the compression of the coronary vessel. The control animals received a treatment with the same volume, i.e. 5 ml/kg of vehicle.

On conscious rats, in the model of arrhythmia following the acute coronary artery occlusion, the compound of Example 15 (having a mixed mechanism of action) showed an antiarrhythmic effect even after oral administration while d-sotalol prolonging repolarization only proved to be inactive in these experiments (Table 9). An other preferable effect of the use of compound of Example 15 is that by using a dose of 25 mg/kg, the heart rate was statistically unchanged during the first 15 minutes of myocardial infarction; in contrast with the heart rate of the untreated control group which was decreased by about 15%.

TABLE 9

Effects on the survival and occurrence of arrhythmias pre-treated with d-sotalol or with the compound of Example 15, respectively, within the first 15 minutes of ischaemia following coronary artery occlusion in the conscious rat model

| Group | N | Survival 15 minutes n/% | Survival 16 hours n/% | Occurrence of arrhythmias, n/% Free | VF | VT | Other | Brady | Arrhythmia Score |
|---|---|---|---|---|---|---|---|---|---|
| Control | 16 | 4/25 | 3/19 | 0/0 | 15/94 | 15/94 | 8/50 | 3/19 | 5.6 ± 0.27 |
| Compound of Example 15 p.o. 25 mg/kg | 16 | 8/50 | 7/44 | 3/19 | 10/63* | 12/75 | 9/56 | 2/12 | 3.94 ± 0.64* |
| d-Sotalol p.o. 25 mg/kg | 7 | 2/29 | 2/29 | 0/0 | 7/100 | 7/100 | 3/43 | 2/29 | 5.71 ± 0.18 |
| d-Sotalol p.o. 50 mg/kg | 10 | 1/10 | 0/0 | 0/0 | 1/100 | 10/100 | 4/40 | 1/10 | 5.90 ± 0.10 |

N: total number of animals in the group; n: number of animals giving an adequate response; Free: no arrhythmia was observed; VF: ventricular fibrillation; VT: ventricular tachycardia; Other: ventricular extrasystole, bigeminy, salvo; Brady: bradycardia. The asterisk means a statistically significant deviation: $P < 0.05$.

The compounds according to the invention can be used in mammals, including humans, for the elimination of cardiac arrhythmias.

For therapeutical purposes, the compounds according to the invention and therapeutically acceptable salts thereof can be used alone or suitably in the form of pharmaceutical compositions. The invention relates also to these compositions.

These pharmaceutical compositions contain an amount of the compound of formula (I) or a therapeutically acceptable salt thereof as active ingredient, which is required for exerting the effect, in admixture with vehicles, fillers, diluting agents and/or other pharmaceutical auxiliaries commonly used in the manufacture of drugs.

Suitable carriers, diluting agents or fillers can be e.g. water, alcohols, gelatine, lactose, saccharose, starch, pectin, magnesium stearate, stearic acid, talc, various oils of animal or plant origin as well as glycols, e.g. propylene glycol or polyethylene glycol. The pharmaceutical auxiliaries are e.g. stabilizers, antioxidants, various natural or synthetic emulsifying, dispersing or wetting agents, colouring agents, aromatizing agents, buffers, disintegrating agents and other substances promoting the biological availability of the active agents.

The pharmaceutical compositions according to the invention may be in the usual pharmaceutical dosage forms. Such usual dosage forms are e.g. oral compositions (administered through an oral route) prepared by using pharmaceutical auxiliaries; these are solid forms such as e.g. tablets, capsules, powders, pills, dragees or granules; or liquid compositions such as syrups, emulsions or suspensions; rectal compositions such as suppositories (which can be administered through a rectal route); and parenteral compositions (administered with avoiding the gastric and intestinal system) such as injections or infusions.

Although the doses of compounds of the present invention required for the therapeutic action depend on the individual state and age of the patient and are determined finally by the physician, for treating diseases accompanied by arrhythmia a daily oral or parenteral, e.g. intravenous, dose of the compound between about 0.1 mg and 5.0 mg, preferably about between 0.1 mg and 2.0 mg calculated for 1 kg of body-weight, can be administered.

Hereinbelow, the compounds according to the invention and the processes for their preparation are illustrated in the following non limiting Examples.

EXAMPLE 1

N-[2-(2,6-Dimethylphenoxy)-1-methylethyl]-N-methyl-2-(4-nitrophenyl)ethylamine-hydrochloride To a solution containing 12.0 g (62 mmol) of N-methyl-2-(2,6-dimethylphenoxy)-1-methylethylamine (BE 626, 725) in 40 ml of isopropanol, 7.13 g (31 mmol) of 4-nitrophenethyl bromide are added and the reaction mixture is boiled under reflux for 5 hours. After evaporation of the solvent, the residue is triturated with 20 ml of ethyl acetate. The precipitated amine hydrobromide is filtered and washed with ethyl acetate. After evaporation of the solution, the crude product (base) obtained is purified by column chromatography (eluent: dichloromethane/methanol=9:0.1). The total yield (HCl salt) is 0.88 g (7.5%) of a white, crystalline product, m.p.: 135–138° C.

$^1$HMR (CDCl$_3$, very dilute solution): 1.15 (m, 3H, C—CH$_3$); 2.25 (s, 6H, Ar-o-CH$_3$); 2.904.20 (m, 10H, O—CH$_2$—CH—N, N—CH$_3$, N—CH$_2$CHrAr); 6.85–7.10 (m, 3H, Ar); 7,48 (d, 2H) and 8.20 (d, 2H) (Ar); 13.0 (br. 1H, NH$^+$).

EXAMPLE 2

N-[2-(2,6-Dimethylphenoxy)ethyl]-N-methyl-2-(4-nitrophenyl)ethylamine hydrochloride The title compound is prepared as described in Example 1, except that N-methyl-2-(2,6-dimethylphenoxy) ethylamine (BE 626,725) is used as starting material, to obtain the title compound in a yield of 30 % (HCl salt) of a white crystalline product, m.p.: 147–149° C.

$^1$HMR (DMSO-$d_6$): 2.22 (s, 6H, Ar—$CH_3$); 2.96 (d, 3H, N—$CH_3$); 3.20–3.80 (m, 6H, $CH_2$—$CH_2$—N—$CH_2$—$CH_2$—Ar); 4.05–4.25 (m, 2H, O—$CH_2$—$CH_2$); 6.80–7.00 (m, 3H, Ar); 7.55 (d, 2H) and 8.15 (d, 2H) (p-nitrophenyl); 11.54 (br. 1H, $NH^+$).

EXAMPLE 3

N-Methyl-N-[2-(2-methylphenoxy)ethyl]-2-(4-nitrophenyl)ethylamine hydrochloride

The title compound is prepared as described in Example 1, except that N-methyl-2-(2-methylphenoxy)ethylamine (Example 43) is used as starting material to obtain 28% (HCl salt) of a white crystalline product, m.p.: 137–138 ° C.

$^1$HMR (DMSO-$d_6$) 2.12 (s, 3H, Ar—$CH_3$); 2.95 (s, 3H, N—$CH_3$); 3.28 (t, 2H, $CH_2$—$CH_2$—Ar); 3.35–3.80 (m, 4H, $CH_2$—N—$CH_2$); 4.42 (t, 2H, O—$CH_2$—$CH_2$); 6.80–7.20 (m, 4H, Ar); 7.60 (d, 2H) and 8.22 (d, 2H) (p-nitrophenyl); 11.25 (br. 1H, $NH^+$).

EXAMPLE 4

(S)-N-[2-(2,6-Dimethylphenoxy)-1-methylethyl]-N-methyl-2-(4-nitrophenyl)ethylamine The title compound is prepared as described in Example 1, except that (S)-N-methyl-2-(2,6-dimethylphenoxy)-1-methylethylamine (Example 47) is used as starting material to give a yield of 17% (base) of an oily substance, which contains 1% of R-enantiomer based on chiral HPLC examination (Chiralcel OJ column); Rf=0.7 (ethyl acetate/methanol =9:1).

EXAMPLE 5

(R)-N-[2-(2,6-Dimethylphenoxy)-1-methylethyl]-N-methyl-2-(4-nitrophenyl)ethylamine The title compound is prepared as described in Example 1, except that (R)-N-methyl-2-(2,6-dimethylphenoxy)-1-methylethylamine (Example 46) is used as starting material to give a yield (base) of 17% of an oil containing no S-enantiomer on the basis of chiral HPLC examination (Chiralcel OJ column); Rf=0.7 (ethyl acetate/methanol= 9:1).

EXAMPLE 6

N-Methyl-N-[2-(2-methylphenoxy)-1-methylethyl]-2-(4-nitrophenyl)ethylamine hydrochloride The title compound is prepared as described in Example 1, except that N-methyl-2-(2-methylphenoxy)-1-methylethylamine (Example 48) is used as starting material to give a yield of 14% (HCl salt) of white crystals, m.p.: 140–142° C.

$^1$HMR (DMSO-$d_6$): 1.45 (m, 3H, C—$CH_3$); 2.10 (s) and 2.20 (s) (total 3H, Ar—$CH_3$); 2.88 (m, 3H, N—$CH_3$); 3.20–3.60 (m, 4H, N—$CH_2$—$CH_2$—Ar); 3.92 (m, 1H, $CH_2$—CH—N); 4.35 (m, 2H, O—$CH_2$—CH); 6.80–7.20 (m, 4H, Ar); 7.60 (m, 2H) and 8.22 (d, 2H) (Ar); 11.20 (br. s, 1H, $NH^+$).

EXAMPLE 7

N-[2-(2,6-Dimethylphenoxy)ethyl]-N-methyl-2-(4-aminophenyl)ethylamine

A solution containing 0.40 g (1.23 mmol) of N-[2-(2,6-dimethylphenoxy)ethyl]-N-methyl-2-(4-nitrophenyl) ethylamine (Example 2) in 7 ml of isopropanol is added to a suspension of 0.1 g of 10% palladium-on-carbon catalyst in 7 ml of isopropanol. The suspension is hydrogenated under atmospheric pressure. After completion of the reaction, the catalyst is filtered and washed with isopropanol. The filtrate is evaporated to constant weight under reduced pressure to obtain 0.37 g of the oily base (76%), Rf=0.35 (ethyl acetate/methanol=9:1).

EXAMPLE 8

N-Methyl-N-[2-(2-methylphenoxy)ethyl]-2-(4-aminophenyl)ethylamine

The title compound is prepared as described in Example 7, except that N-[2-(2-methylphenoxy)ethyl]-N-methyl-2-(4-nitrophenyl)ethylamine (Example 3) is used as starting material to obtain a yield of 82% of the base (oil), Rf=0.35 (ethyl acetate/methanol=9:1).

EXAMPLE 9

N-[2-(2,6-Dimethylphenoxy)-1-methylethyl]-N-methyl-2-(4-aminophenyl)ethylamine

The title compound is prepared as described in Example 7, except that N-[2-(2,6-dimethylphenoxy)-1-methylethyl]-N-methyl-2-(4-nitrophenyl)ethylamine (Example 1) is used as starting material to give a yield of 90% of the oily base.

$^1$HMR ($CDCl_3$): 1.25 (d, 3H, C—$CH_3$); 2.32 (s, 6H, Ar—$CH_3$); 2.48 (s, 3H, N—$CH_3$); 2.65–2.85 (m, 4H, N—$CH_2$—$CH_2$—Ar); 3.28 (m, 1H, $CH_2$—CH—N); 3.2–3.8 (br. s, 2H, $NH_2$); 3.65 (dd, J=9.2 and 6.7 Hz, 1H) and 3.92 (dd, J=9.2 and 5.7 Hz, 1H) (O—$CH_2$—CH); 6.66 (d, 2H, Ar); 6.9–7.10 (m, 5H, Ar).

EXAMPLE 10

(S)-N-[2-(2,6-Dimethylphenoxy)-1-methylethyl]-N-methyl-2-(4-aminophenyl)ethylamine The title compound is prepared as described in Example 7, except that (S)-N-[2-(2,6-dimethylphenoxy)-1-methylethyl]-N-methyl-2-(4-nitrophenyl)ethylamine (Example 4) is used as starting material to give a yield of 93% of a white oil (base), which contains 1 to 2% of R-enantiomer on the basis of chiral HPLC examination (Chiralcel OJ column); Rf=0.35 (ethyl acetate/methanol= 9:1).

EXAMPLE 11

(R)-N-[2-(2,6-Dimethylphenoxy)-1-methylethyl]-N-methyl-2-(4-aminophenyl)ethylamine The title compound is prepared as described in Example 7, except that (R)-N-[2-(2,6-dimethylphenoxy)-1-methylethyl]-N-methyl-2-(4-nitrophenyl)ethylamine (Example 5) is used as starting material to obtain a yield of 89% of the white oily base, which contains 1% of S-enantiomer on the basis of chiral HPLC examination (Chiralcel OJ column); Rf=0.35 (ethyl acetatelmethanol= 9:1).

EXAMPLE 12

N-Methyl-N-[2-(2-methylphenoxy)-1-methylethyl]-2-(4-aminophenyl)ethylamine

The title compound is prepared as described in Example 7, except that N-methyl-N-[2-(2-methylphenoxy)-1-methylethyl]-2-(4-nitrophenyl)ethylamine (Example 6) is used as starting material to give a yield of 89% of the oily base.

$^1$HMR (CDCl$_3$): 1.16 (d, 3H, C—CH$_3$); 2.20 (s, 3H, Ar—CH$_3$); 2.40 (s, 3H, N—CH$_3$); 2.60–2.80 (m, 4H, N—CH$_2$—CH$_2$—Ar); 3.30–3.70 (br. s, 2H, NH$_2$); 3.70 (m, 1H, CH$_2$—CH$_2$—N); 3.82 (dd, 1H) and 4.02 (dd, 1H) (O—CH$_2$—CH); 6.60 (d, 2H) and 7.00 (d, 2H) (p-aminophenyl); 6.72–6.90 (m, 2H) and 7.08–7.20 (m, 2H) (Ar).

EXAMPLE 13

N-[4-[2-[N-Methyl-N-[2-(2,6-dimethylphenoxy)ethyl]amino]ethyl]phenyl]methanesulfonamide hydrochloride To a solution containing 1.44 g (4.82 mmol) of N-[2-(2,6-dimethylphenoxy)ethyl]-N-methyl-2-(4-aminophenyl)ethylamine (Example 7) in 50 ml of dichloromethane, 0.50 g (4.95 mmol) of triethylamine is added then 0.63 g (5.5 mmol) of methanesulfonyl chloride is dropwise added to the solution cooled to 0° C. at the same temperature. After further stirring the reaction mixture at 0° C. for 1 hour and washing with 30 ml of saturated sodium hydrogen carbonate solution, the aqueous phase is extracted twice with 20 ml of dichloromethane each. The combined organic phase is washed twice with 30 ml of water each, dried and evaporated to give a yield of 0.44 g (94%) of the oily base. The yield of HCl salt is 0.244 g (47%) of white crystals, m.p.: 168–169 ° C.

$^1$HMR (DMSO-d$_6$): 2.25 (s, 6H, Ar—CH$_3$); 2.95 (s, 6H, N—CH$_3$ and S—CH$_3$ overlapping); 3.10 (t, 2H, CH$_2$—CH$_2$—Ar); 3.25–3.75 (m, 4H, CH$_2$—N—CH$_2$); 4.15 (t, 2H, O—CH$_2$—CH$_2$); 6.85–7.05 (m, 3H, Ar); 7.14 (d, 2H) and 7.24 (d, 2H) (4-methanesulfonamido-phenyl); 9.75 (s, 1H, Ar—NH—S); 11.20 (br. 1H, NH$^+$).

EXAMPLE 14

N-[4-[2-[N-Methyl-N-[2-(2-methylphenoxy)ethyl]amino]ethyl]-phenyl]methanesulfonamide hydrochloride The title compound is prepared as described in Example 13, except that N-methyl-N-[2-(2-methylphenoxy)ethyl]-2-(4-aminophenyl)ethylamine (Example 8) is used as starting material to give a yield of 71% (HCl salt) of white crystals, m.p.: 180–181° C.

$^1$HMR (DMSO-d$_6$): 2.15 (s, 3H, Ar—CH$_3$); 2.90 (d, 3H, N—CH$_3$); 2.95 (s, 3H, S—CH$_3$); 3.10 (t, 2H, CH$_2$—CH$_2$—Ar); 3.25–3.80 (m, 4H, CH$_2$—N—CH$_2$); 4.44 (t, 2H, O—CH$_2$—CH$_2$); 6.80–7.00 (m, 2H, Ar) and 7.15–7.30 (m, 6H) (Ar); 9.75 (s, 1H, Ar—NH—S); 11.20 (br. 1H, NH$^+$).

EXAMPLE 15

N-[4-[2-[N-Methyl-N-[2-(2,6-dimethylphenoxy)-1-methylethyl]amino]ethyl]phenyl]methanesulfonamide hydrochloride The title product is prepared as described in Example 13, except that N-[2-(2,6-dimethylphenoxy)-1-methylethyl]-N-methyl-2-(4-aminophenyl)ethylamine (Example 9) is used as starting material to obtain a yield of 56% (HCl salt) of white crystals, m.p.: 224–227° C.

$^1$HMR (DMSO-d$_6$, at room temperature): 1.45 (m, 3H, C—CH$_3$); 2.28 (s, 6H, Ar-o-CH$_3$); 2.90 (m, 3H, N—CH$_3$); 2.96 (s, 3H, S—CH$_3$); 3.00–3.50 (m, 4H, N—CH$_2$—CH$_2$—Ar); 3.90 (m, 1H, CH$_2$—CH—N); 3.98– 4.16 (m, 2H, O—CH$_2$—CH); 6.90–7.10 (m, 3H, Ar); 7.14–7.32 (m, 4H, Ar); 9.75 (s, 1H, Ar—NH—S); 10.90 (br. s, 1H, NH$^+$).

EXAMPLE 16

(S)-N-[4-[2-[N-Methyl-N-[2-(2,6-dimethylphenoxy)-1-methylethyl]amino]ethyl]phenyl]methanesulfonamide hydrochloride The title compound is prepared as described in Example 13, except that (S)-N-[2-(2,6-dimethylphenoxy)-1-methylethyl]-N-methyl-2-(4-aminophenyl)ethylamine (Example 10) is used as starting material to give a yield of 63% (HCl salt) of white crystals, m.p.: 192–193° C.

On the basis of chiral HPLC analysis (Chiralcel OJ column), this product does not contain R-enantiomer.

$^1$HMR (DMSO-d$_6$, at room temperature): 1.45 (m, 3H, C—CH$_3$); 2.28 (s, 6H, Ar-o-CH$_3$); 2.90 (m, 3H, N—CH$_3$); 2.96 (s, 3H, S—CH$_3$); 3.00–3.50 (m, 4H, N—CH$_2$—CH$_2$—Ar); 3.90 (m, 1H, CH$_2$—CH—N); 3.98–4.16 (m, 2H, O—CH$_2$—CH); 6.90–7.10 (m, 3H, Ar); 7.14–7.32 (m, 4H, Ar); 9.70 (s, 1H, Ar—NH—S); 10.75 (br.s, 1H, NH$^+$).

$^1$HMR (DMSO-d$_6$, 100° C.): 1.45 (d, 3H, C—CH$_3$); 2.28 (s, 6H, Ar-o-CH$_3$); 2.88 (s, 3H, N—CH$_3$); 2.96 (s, 3H, S—CH$_3$); 3.00–3.50 (m, 4H, N—CH$_2$—CH$_2$—Ar); 3.85 (m, 1H, CH$_2$—CH—N); 4.04 (dd, J=10.6 and 5.1 Hz, 1H) and 4.14 (dd, J=10.6 and 5.6 Hz, 1H)(O—CH$_2$—CH); 6.90–7.06 (m, 3H, Ar); 7.16–7.30 (m, 4H, Ar); 9.35 (s, 1H, Ar—NH—S); 11.00 (br.s, 1H, NH$^+$).

EXAMPLE 17

(R)-N-[4-[2-[N-Methyl-N-[2-(2,6-dimethylphenoxy)-1-methylethyl]amino]ethyl]phenyl]methanesulfonamide hydrochloride The title product is prepared as described in Example 13, except that (R)-N-[2-(2,6-dimethylphenoxy)-1-methylethyl]-N-methyl-2-(4-aminophenyl)ethylamine (Example 11) is used as starting material to obtain a yield of 55% (HCl salt); white crystals, m.p.: 190–191° C.

On the basis of chiral HPLC analysis (Chiralcel OJ column), this product does not contain S-enantiomer.

$^1$HMR (DMSO-d$_6$, at room temperature): 1.45 (m, 3H, C—CH$_3$); 2.28 (s, 6H, Ar-o-CH$_3$); 2.90 (m, 3H, N—CH$_3$); 2.96 (s, 3H, S—CH$_3$); 3.00–3.50 (m, 4H, N—CH$_2$—CH$_2$—Ar); 3.90 (m, 1H, CH$_2$—CH—N); 3.98–4.16 (m, 2H, O—CH$_2$—CH); 6.90–7.10 (m, 3H, Ar); 7.14–7.32 (m, 4H, Ar); 9.70 (s, 1H, Ar—NH—S); 10.75 (br. s, 1H, NH$^+$).

EXAMPLE 18

N-[4-[2-[N-Methyl-N-[2-(2-methylphenoxy)-1-methylethyl]-amino]ethyl]phenyl]methanesulfonamide hydrochloride The title compound is prepared as described in Example 13, except that N-methyl-N-[2-(2-methylphenoxy)-1-methylethyl]-2-(4-aminophenyl)ethylamine (Example 12) is used as starting material to give a yield of 60% (HCl salt) of white crystals, m.p.: 165–167° C.

$^1$HMR (DMSO-d$_6$): 1.34–1.52 (m, 3H, C—CH$_3$); 2.10 (s) and 2.20 (s) (total 3H, Ar—CH$_3$); 2.85 (m, 3H, N—CH$_3$); 2.96 (s, 3H, S—CH$_3$); 3.05–3.50 (m, 4H, N—CH$_2$—CH$_2$—Ar); 3.94 (m, 1H, CH$_2$—CH—N); 4.20–4.40 (m, 2H, O—CH$_2$—CH); 6.80–7.00 (m, 2H) and 7.10–7.35 (m, 6H) (Ar); 9.72 (s, 1H, Ar—NH—S); 10.70–11.00 (br. 1H, NH$^+$).

EXAMPLE 19

N-[4-[2-[N-Methyl-N-[2-(2,3-dimethylphenoxy)-1-methylethyl]amino]ethyl]phenyl]methanesulfonamide hydrochloride To a solution containing 0.82 g (2 mmol) of N-[2-(2,3-dimethylphenoxy)-1-methylethyl]-N-methyl-2-(4-methanesulfonamidophenyl)acetamide (Example 50) in 20 ml of abs. tetrahydrofuran, 0.10 g of lithium aluminium hydride (LAH) is added in small portions under stirring, then the mixture is boiled about one hour in order to complete the reaction. The progress of reaction is followed by thin-layer chromatography (TLC). After completion, the excess reagent is decomposed by adding ethyl acetate, then 10% sodium hydroxide solution is added and the mixture is extracted with ethyl acetate. The combined organic phase is washed with water, then extracted with 2 N aqueous hydrochloric acid. The acidic phase is alkalinized to pH 9 by adding 10% sodium hydroxide and then extracted with ethyl acetate. The ethyl acetate extract is washed with water, dried and evaporated under reduced pressure to obtain 0.56 g of a thick oil as residue. This crude product is purified, if desired, by column chromatography by using a mixture of hexane and ethyl acetate of a ratio of 2:1 or 1:1, respectively. The HCl salt is obtained in a yield of 0.38 g (45%) as amorphous white flakes.

$^1$HMR (DMSO-d$_6$): 1.40–1.50 (m, 3H, C—CH$_3$); 2.00 (s), 2.08 (s) and 2.22 (s) (totally 6H, Ar—CH$_3$); 2.80–2.90 (m, 3H, N—CH$_3$); 2.95 (s, 3H, S—CH$_3$); 3.00–3.50 (m, 4H, N—CH$_2$—CH$_2$—Ar); 3.92 (m, 1H, CH$_2$—CH—N); 4.25–4.35 (m, 2H, O—CH$_2$—CH); 6.75–7.30 (m, 7H, Ar); 9.75 (s, 1H, Ar—NH—S); 10.8–11.1 (m, 1H, NH$^+$).

EXAMPLE 20

N-[4-[2-[N-Methyl-N-[2-(2,5-dimethylphenoxy)-1-methylethyl]amino]ethyl]phenyl]methanesulfonamide hydrochloride The title compound is prepared as described in Example 19, except that N-[2-(2,5-dimethylphenoxy)-1-methylethyl]-N-methyl-2-(4-methanesulfonamido-phenyl)acetamide (Example 51) is used as starting material to yield 40% of the HCl salt, which is an amorphous white precipitate.

$^1$HMR (DMSO-d$_6$): 1.40–1.50 (m, 3H, C—CH$_3$); 2.00 (s), 2.10 (s), 2.25 (s) and 2.26 (s) (total 6H, Ar—CH$_3$); 2.80–2.90 (m, 3H, N—CH$_3$); 2.95 (s, 3H, S—CH$_3$); 3.00–3.50 (m, 4H, N—CH$_2$—CH$_2$—Ar); 3.92 (m, 1H, CH$_2$—CH—N); 4.20–4.35 (m, 2H, O—CH$_2$—CH); 6.60–7.30 (m, 7H, Ar); 9.75 (s, 1H, Ar—NH—S); 10.65–11.00 (m, 1H, NH$^+$).

EXAMPLE 21

N-[4-[2-[N-Methyl-N-[2-(2-chlorophenoxy)-1-methylethyl]-amino]ethyl]phenyl]methanesulfonamide hydrogen fumarate The title product is prepared as described in Example 19, except that N-[2-(2-chlorophenoxy)-1-methylethyl]-N-methyl-2-(4-methanesulfonamido-phenyl)acetamide (Example 52) is used as starting material to give the fumarate salt in a yield of 46%, m.p.: 152–153° C.

$^1$HMR (DMSO-d$_6$): 1.12 (d, 3H, C—CH$_3$); 2.40 (s, 3H, N—CH$_3$); 2.60–2.90 (m, 4H, N—CH$_2$—CH$_2$—Ar); 2.92 (s, 3H, s-CH$_3$); 3.24 (m, 1H, CH$_2$—CH—N); 3.96 (dd, J=10.0 and 6.0 Hz, 1H) and 4.10 (dd, j=10.0 and 5.6 Hz, 1H) (O—CH$_2$—CH); 6.60 (s, 2H, fumaric acid); 6.90–7.45 (m, 7H, Ar); 9.58 (s, 1H, Ar—NH—S).

EXAMPLE 22

N-[4-[2-[N-[2-(2,6-Dimethylphenoxy)-1-methylethyl]amino]-ethyl]phenyl]methanesulfonamide hydrochloride A mixture containing 0.58 g (2.08 mmol) of 2-(2,6-dimethylphenoxy)-1-methylethylamine (U.S. Pat. No. 3,659,019) and 0.3 g (1.08 mmol) of N-[4-(2-bromoethyl)phenyl]methanesulfonamide (GB 971,041) is melted at 120° C. for 4 hours. The mixture obtained is purified by column chromatography, eluted with a mixture of dichloromethane and methanol of 9:0.2 ratio. The obtained product is triturated with hexane and filtered to give the base in a yield of 64%; white crystals, m.p.: 81–84° C.

$^1$HMR (CDCl$_3$): 1.14 (d, 3H, C—CH$_3$); 2.18 (s, 6H, Ar—CH$_3$); 2.86 (s, 3H, S—CH$_3$); 2.70–3.20 (m, 5H, CH$_2$—CH—N—CH$_2$—CH$_2$—Ar); 3.64 (d, H, O—CH$_2$—CH); 4.0–4.6 (br., 2H, NH); 6.80–7.00 (m, 3H, Ar); 7.10–7.25 (m, 4H, Ar).

The HCl salt is obtained in a yield of 60%; white crystals, m.p.: 10–21 1° C.

EXAMPLE 23

N-[4-[2-[N-Methyl-N-[3-(2,6-dimethylphenoxy)propyl]amino]-ethyl]phenyl]methanesulfonamide hydrochloride The title compound is prepared as described in example 22, except that N-methyl-4-(2,6-dimethylphenoxy)propylamine (BE 626,725) is used as starting material to obtain the oily base in a yield of 59%.

$^1$HMR (CDCl$_3$, base): 1.96 (m, 2H, CH$_2$—CH$_2$—CH$_2$); 2.26 (s, 6H, Ar—CH$_3$); 2.35 (s, 3H, N—CH$_3$); 2.58–2.82 (m, 6H, CH$_2$—CH$_2$—N—CH$_2$—CH$_2$—Ar); 2.92 (s, 3H, S—CH$_3$); 3.75 (t, 2H, O—CH$_2$—CH$_2$); 6.00–6.60 (1H, NH); 6.82–7.02 (m, 3H, 2,6-dimethylphenoxy group); 7.16 (s, 4H, 4-methanesulfonamido-phenyl group).

The HCl salt is obtained in a yield of 49%; white crystals, m.p.: 115–117° C.

EXAMPLE 24

N-[4-[2-[N-Methyl-N-[4-(2,6-dimethylphenoxy)butyl]amino]ethyl]phenyl]methanesulfonamide hydrochloride The title compound is prepared as described in Example 22, except that N-methyl-4-(2,6-dimethylphenoxy)butylamine (BE 626,725) is used as starting material to obtain the oily base in a yield of 57%.

$^1$HMR (CDCl$_3$, base): 1.62–1.88 (m, 4H, CH$_2$—CH$_2$—CH$_2$—CH$_2$); 2.26 (s, 6H, Ar—CH$_3$), 2.32 (s, 3H, N—CH$_3$); 2.45–2.85 (m, 6H, CH$_2$—CH$_2$—N—CH$_2$—CH$_2$—Ar); 2.95 (s, 3H, S—CH$_3$); 3.75 (t, 2H, O—CH$_2$—CH$_2$); 5.30–6.30 (1H, NH); 6.82–7.02 (m, 3H, 2,6-dimethylphenoxy group); 7.16 (s, 4H, 4-methanesulfonamido-phenyl group).

The HCl salt is obtained in a yield of 42.0%; strongly hygroscopic off-white crystals.

EXAMPLE 25

N-[4-[2-[N-Methyl-N-[2-(2,6-dimethylphenoxy)-1-methylethyl]amino]ethyl]phenyl]benzamide hydrochloride To a solution containing 0.2 g (0.64 mmol) of N-[2-(2,6-dimethylphenoxy)-1-methylethyl]-N-methyl-2-(4-aminophenyl)ethylamine (Example 9) in 1.7 ml of acetonitrile, 0.11 ml (0.768 mmol) of triethylamine is added, then 0.082 ml (7.04 mmol) of benzoyl chloride is added under stirring. The reaction mixture is stirred at room temperature (cooled or heated, if necessary). After completion, the reaction mixture is evaporated under reduced pressure, 10 ml of water are added to the evaporation residue, and the pH value is adjusted to alkaline, if necessary, by adding sodium hydroxide solution The product is extracted three times with 20 ml of ethyl acetate each. The organic phase is washed with 50 ml of water, dried and evaporated to give 0.24 g (90%) of an oil.

$^1$HMR (CDCl$_3$): 1.16 (d, 3H, C—CH$_3$); 2.25 (s, 6H, Ar—CH$_3$); 2.45 (s, 3H, N—CH$_3$); 2.65–2.85 (m, 4H, N—CH$_2$CH$_2$—Ar); 3.26 (sx, 1H, CH$_2$—CH—N); 3.64 (dd, J=9.5 and 6.1 Hz, 1H) and 3.84 (dd, J=9.5 and 5.6 Hz, 1H) (O—CH$_2$—CH); 6.80–7.00 (m, 3H, Ar); 7.10 (d, 2H) and 7.80 (d, 2H) (p-benzoylamino-phenyl group); 7.25–7.45 (m, 3H) and 7.56 (d, 2H) (benzoyl group); 8.70 (s, 1H, NH).

The HCl salt is obtained in a yield of 0.19 g (66%); white crystals, m.p.: 108–111° C.

EXAMPLE 26

N-[4-[2-[N-Methyl-N-[2-(2,6-dimethylphenoxy)-1-methylethyl]amino]ethyl]phenyl]acetamide sesquihydrochloride monohydrate The title compound is prepared as described in Example 25, except that acetyl chloride is used as acylating reagent to give the salt in a yield of 68%; white crystals, m.p.: 104–106° C.

Analysis for C$_{22}$H$_{30}$N$_2$O$_2$.1.5HCl.H$_2$O (molecular weight 427.20):

calculated: C 61.85; H 7.90; N 6.56; Cl 12.44; H$_2$O 4.22%;

found: C 61.79; H 7.74; N 6.34; Cl 13.96; H$_2$O 4.70%.

$^1$HMR (DMSO-d$_6$): 1.40–1.50 (m, 3H, C—CH$_3$); 2.05 (s, 3H, Ac); 2.15 (s, 6H, Ar—CH$_3$); 2.80–2.90 (m, 3H, N—CH$_3$); 2.90–3.60 (m, 4H, N—CH$_2$—CH$_2$—Ar); 3.85 (m, 1H, CH$_2$—CH—N); 4.05–4.15 (m, 2H, O—CH$_2$—CH); 6.80–7.05 (m, 3H, Ar); 7.15–7.25 (m, 2H) and 7.55–7.65 (m, 2H) (p-acetamino-phenyl); 10.15 (s, 1H, Ar—NH—CO); 11.22 (br. 1H, NH$^+$).

EXAMPLE 27

1-Methyl-3-[4-[2-[N-methyl-N-[2-(2,6-dimethylphenoxy)-1-methylethyl]amino]ethyl]phenyl] thiourea sesquihydrochloride hemihydrate To a solution containing 0.30 g (0.96 mmol) of N-[2-(2,6-di-methylphenoxy)-1-methyl ethyl]-N-methyl-2-(4-aminophenyl)ethyl amine (Example 9) in 2.5 ml of dioxane, 0.077 g (1.05 mmol) of methyl isothiocyanate is added. The reaction mixture is stirred at room temperature (and, if necessary, heated or further methyl isothiocyanate is added). After completion of the reaction, the solvent is evaporated under reduced pressure. The evaporation residue is purified by column chromatography or triturated with a little amount of n-hexane, decanted, 10 ml of water are added to the oil, the pH value is adjusted to alkaline by adding sodium hydroxide solution (when necessary), then the product is extracted three times with 20 ml of ethyl acetate each. The combined organic phase is washed with 50 ml of water, dried and evaporated to give 0.11 g (48%) of the oily base.

$^1$HMR (CDCl$_3$): 1.16 (d, 3H, C—CH$_3$); 2.26 (s, 6H, Ar—CH$_3$); 2.42 (s, 3H, N—CH$_3$); 2.65–2.90 (m, 4H, N—CH$_2$—CH$_2$—Ar); 3.10 (d, 3H, NH—CH$_3$); 3.25 (m, 1H, CH$_2$—CH—N); 3.62 (dd, J=9.3 and 6.1 Hz, 1H); and 3.85 (dd, J=9.3 and 5.9 Hz, 1H) (O—CH$_2$—CH); 6.04 (d, CS—NH—CH$_3$); 6.85–7.00 (m, 3H, Ar); 7.12 (d, 2H) and 7.26 (d, 2H) (p-thioureido-phenyl group), 8.00 (s, 1H, Ar—NH-CS).

The salt is obtained in a yield of 0.136 g (31%); hygroscopic white crystals, m.p.: 120–122° C.

Analysis for C$_{22}$H$_{31}$N$_3$OS 1.5HCl.0.5H$_2$O (molecular weight 449.27):

calculated: C 58.82; H 7.52; N 9.35%;

found: C 58.87; H 7.61; N 8.66%.

EXAMPLE 28

1-Ethyl-3-[4-[2-[N-methyl-N-[2-(2,6-dimethylphenoxy)-1-methylethyl]amino]ethyl]phenyl]urea The title compound is prepared as described in Example 27, except that ethyl isocyanate is used as reagent to obtain the oily base in a yield of 59%.

$^1$HMR (CDCl$_3$): 1.05 (t, 3H, CH$_2$—CH$_3$); 1.15 (d, 3H, CH—CH$_3$); 2.28 (s, 6H, Ar—CH$_3$); 2.40 (s, 3H, N—CH$_3$); 2.60–2.80 (m, 4H, N—CH$_2$—CH$_2$—Ar); 3.08–3.28 (m, 3H, N—CH$_2$—CH$_3$ and CH$_2$—CH—N); 3.58 (dd, J 9.1 and 6.5 Hz, 1H) and 3.86 (dd, J=9.1 and 5.8 Hz, 1H) (O—CH$_2$—CH); 6.00 (t, 1H, CO—NH—CH$_2$); 6.82–7.02 (m, 3H, o-dimethylphenoxy group); 7.05 (d, 2H) and 7.22 (d, 2H) (p-ethylureido-phenyl group); 7.90 (s, 1H, Ar—NH—CO).

EXAMPLE 29

N-[2-(2,6-Dimethylphenoxy)-1-methylethyl]-N-methyl-2-[4-(N'-ethylamino)phenyl]ethylamine The title compound is prepared as described in Example 19, except that N-[4-[2-[N-methyl-N-[2-(2,6-dimethylphenoxy)-1-methylethyl]amino]ethyl]phenyl] acetamide (Example 26) is used as starting material to give the oily base in a yield of 60%.

$^1$HMR (CDCl$_3$, base): 1.17 (d, 3H, CH—CH$_3$); 1.21 (t, 3H, CH$_2$—CH$_3$); 2.30 (s, 6H, Ar—CH$_3$); 2.42 (s, 3H, N—CH$_3$); 2.60–2.80 (m, 4H, N—CH$_2$—CH$_2$—Ar); 3.11 (q, 2H, N—CH$_2$—CH$_3$); 3.01 (m, 1H, CH$_2$—CH—N); 3.59 (dd, J=9.1 and 6.7 Hz, 1H) and 3.86 (dd, J=9.1 and 5.6 Hz, 1H) (O—CH$_2$—CH); 6.54 (d, 2H) and 7.01 (d, 2H) (p-ethylamino-phenyl group); 6.86–7.06 (m, 3H, o-dimethylpheenoxy group).

EXAMPLE 30

N-[4-[2-[N-Propyl-N-[2-(2,6-dimethylphenoxy)ethyl] amino]ethyl]phenyl]methanesulfonamide The title compound is prepared as described in Example 22, except that N-[2-(2,6-dimethylphenoxy)ethyl]propylamine (EP 152,131) is used as starting material to obtain the oily base in a yield of 25%.

$^1$HMR (CDCl$_3$, base): 0.88 (t, 3H, N—CH$_2$—CH$_2$—CH$_3$); 1.52 (m, 2H, N—CH$_2$—CH$_2$—CH$_3$); 2.27 (s, 6H, Ar—CH$_3$); 2.60 (t, 2H, N—CH$_2$—CH$_2$—CH$_3$); 2.70–2.90 (m, 4H, N—CH$_2$—CH$_2$—Ar); 2.95 (s, 3H, S—CH$_3$); 2.99 (t, 2H, O—CH$_2$—CH$_2$—N); 3.85 (t, 2H, O—CH$_2$—CH$_2$—N); 6.85–7.05 (m, 3H, 2,6-dimethylphenoxy group); 7.16 (s, 4H, p-methanesulfonamidophenyl group).

EXAMPLE 31

N-[4-[2-[N-Methyl-N-[2-(2-isopropylphenoxy)-1-methylethyl]-amino]ethyl]phenyl]methanesulfonamide hydrochloride The title compound is prepared as described in Example 22, except that N-methyl-2-(2-isopropylphenoxy)-1-methylethylamine (Example 49) is used as starting substance to give the oily base in a yield of 52%.

$^1$HMR (CDCl$_3$, base): 1.12–1.22 (m, 9H, CH—CH$_3$ and Ar—CH—(CH$_3$)$_2$); 2.41 (s, 31H, N—CH$_3$); 2.70–2.80 (m, 41H, N—CH$_2$—CH$_2$—Ar); 3.15–3.40 (m, 2H, CH$_2$—CH—N and Ar—CH—(CH$_3$)$_2$); 3.81 (dd, J=9.3 and 6.4 Hz, 1H) and 4.00 (dd, J=9.3 and 5.4 Hz, 1H) (O—CH$_2$—CH); 6.77 (dd, J=8.0 and 1.0 Hz, 1H); 6.92 (td, J=7.5 and 1.0 Hz, 1H); 7.10–7.25 (m, 6H) (Ar).

The HCl salt is obtained in a total yield of 38%; white crystals, m.p.: 86–89° C.

Preparation of the Starting Materials

EXAMPLE 32

4-(Methanesulfonamido)phenylacetic acid

In a solution containing 5.44 g (53 mmol) of sodium carbonate in 36 ml of water, 3.2 g (20 mmol) of 4-aminophenylacetic acid are dissolved, 1.7 ml (2.48 g, 22 mmol) of methanesulfonyl chloride are added in one portion and the mixture is heated at 85° C. for 4 hours. After cooling down and acidifying the reaction mixture to pH 3 with concentrated hydrochloric acid, the mixture is cooled in the refrigerator overnight, filtered, washed with water and dried to obtain 2.7 g of a crude product, which is recrystallized from 6 ml of hot water to give 2.40 g of the title substance as beige laminar crystals; yield: 53%, m.p.: 145–147° C.

$^1$HMR (DMSO-d$_6$): 2.95 (s, 3H, S—CH$_3$); 3.48 (s, 2H, Ar—CH$_2$—CO); 7.10 (d, 2H) and 7.18 (d, 2H) (Ar); 9.65 (br, 1H, NH); 12.25 (br, 1H, COOH).

Preparation of Compounds of Formula (V)

EXAMPLE 33

1-(2,5-Dimethylphenoxy)-2-propanal

To a solution containing 3.67 g (30 mmol) of 2,5-dimethylphenol in 16 ml of 96% ethanol, 2.61 g (45 mmol) of propylene oxide and 0.44 g (3.2 mmol) of potassium carbonate are added, then the suspension formed is boiled while stirring for 6 hours. After filtration of the reaction mixture and washing with ethanol, the solvent is evaporated under reduced pressure. The crude product (obtained in a yield of 100%) is purified by distillation under reduced pressure, when necessary. The yield is 85% of a colourless liquid; boiling point 104–107° C./0.26 kPa; Rf=0.1 (toluene).

EXAMPLE 34

(R)-1-(2,6-Dimethylphenoxy)-2-propanol

The title compound is prepared as described in Example 33, except that 2,6-dimethylphenol and R(+)-propylene oxide are used as starting materials to give the crude product in a yield of 100%. Based on chiral HPLC analysis (Chiralcel OJ column), this product is of 74.4 % chemical purity, without S-enantiomer content.

EXAMPLE 35

(S)-1-(2,6-Dimethylphenoxy)-2-propanol

The title compound is prepared as described in Example 33, except that 2,6-dimethylphenol and S(-)-propylene oxide are used as starting materials to give a crude product in a yield of 100%. Based on chiral HPLC analysis (Chiralcel OJ column), this product is of 78% chemical purity, without R-enantiomer content.

EXAMPLE 36

1-(2-Isopropylphenoxy)-2-propanol

The title compound is prepared as described in Example 33, except that 2-isopropylphenol and propylene oxide are used as starting materials to give the crude product in a yield of 100%; Rf=0.1 (toluene).

Preparation of Compounds of Formula (IV)

General Method:

To a solution containing 30 mmol of the compound of formula (V) in 10 ml of pyridine, 7.63 g (40 mmol) of 4-toluenesulfonyl chloride are added at room temperature while stirring. After stirring for 3 hours, the reaction mixture is poured onto 55 ml of water. The product is extracted twice with 40 ml of ethyl acetate each, the organic phase is washed twice with 25 ml of 2 N hydrochloric acid each, twice with 20 ml of water each, twice with 20 ml of 1 N sodium carbonate solution each and finally three times with 20 ml of water each, and after evaporation of the solvent, if necessary, the evaporation residue is crystallized from a mixture of hexane and diisopropyl ether.

By using the above general method, the following compounds of formula (IV), wherein R$^1$, R$^2$ and R$^3$ are as given in Table 10, n and m are 0 and X means 4-toluenesulfonyloxy group, were prepared.

TABLE 10

| Example | $R^1$ | $R^2$ | $R^3$ | Starting substance | Yield (%) | M.p. (° C.) | Others |
|---|---|---|---|---|---|---|---|
| 37 | 2-CH$_3$ | 5-CH$_3$ | CH$_3$ | 1-(2,5-dimethylphenoxy)-2-propanol (Example 33) | 60 | 58–59 | |
| 38 | 2-CH$_3$ | 3-CH$_3$ | CH$_3$ | 1-(2,3-dimethylphenoxy)-2-propanol[a] | 80 | 71–72 | |
| 39 | 2-CH$_3$ | 6-CH$_3$ | (R)-CH$_3$ | (R)-1-(2,6-dimethylphenoxy)-2-propanol (Example 34) | 64 | 78–80 | $\alpha_D^{20}$ = +33.8° (c = 1, methanol) |
| 40 | 2-CH$_3$ | 6-CH$_3$ | (S)-CH$_3$ | (S)-1-(2,6-dimethylphenoxy)-2-propanol (Example 35) | 64 | 78–80 | $\alpha_D^{20}$ = −33.8° (c = 1, methanol) |
| 41 | 2-CH$_3$ | H | CH$_3$ | 1-(2-methylphenoxy)-2-propanol[b] | 79 | 51–62 protracted | |
| 42 | 2-CH(CH$_3$)$_2$ | H | CH$_3$ | 1-(2-isopropylphenoxy)-2-propanol (Example 36) | 29 | 36–37 | |

[a]S. Honma et al., Chem. Pharm. Bull. 25, 1843–1850 (1977)
[b]FR 1,386,347

Preparation of Compounds of Formula (II)

General Method:

After reacting 30 mmol of suitably substituted compounds of formula (IV) (wherein X means halogen or 4-toluenesulfonyloxy group) with 60 ml of 33% ethanolic methylamine or substituted amine at 100 ° C. in a closed tube for 5 hours, the reaction mixture is evaporated. The obtained oil is taken up in 40 ml of 2 N aqueous hydrochloric acid and washed with 10 ml of ethyl acetate. The pH value of the aqueous phase is adjusted to 10 by adding 5 N sodium hydroxide solution, then the mixture is extracted three times with 50 ml of dichloromethane each. The organic phase is washed twice with 40 ml of water each, dried, filtered, then the solution is evaporated. The obtained oil is transformed to a salt or purified by distillation under reduced pressure or used further in crude form.

The following compounds of formula (II), wherein $R^1$, $R^2$, $R^3$ and R are as defined in Table 11, and n and m are 0, were prepared by following the above general method.

20 ml of N,N-dimethylformamide (DMF) 0.46 ml (0.42 g, 4,2 mmol) of 4-methylmorpholine is added, the mixture is cooled to −10° C. and 0.65 ml (0.70 g, 5 mmol) of isobutyl chloroformate is added. After 10 minutes a solution containing 0.68 g (3.5 mmol) of N-methyl-2-(2,3-dimethylphenoxy)-1-methylethylamine (Example 44) in 3 ml of DMF pre-cooled to −10° C. is added, then the pH value of the mixture is adjusted to 8.5 by adding triethylamine. The reaction mixture is stirred at −10° C. for 1 hour, then at 0° C. for 1 hour. Then, the solvent is evaporated under reduced pressure and the solid residue is alkalinized by adding aqueous ammonia solution and distributed between water and ethyl acetate. The aqueous phase is washed twice with ethyl acetate, the combined organic phase is washed once with water, dried over sodium sulphate and evaporated. Thus, 1.13 g of the title substance are obtained as an amorphous substance, which is suitable to the next step without further purification. Yield: 80%.

$^1$HMR (CDCl$_3$): 1.18–1.38 (m, 3H, C—CH$_3$); 2.10–2.20 (m, 3H) and 2.25–2.35 (m, 3H) (Ar—CH$_3$); 2.85–3.05 (m,

TABLE 11

| Example | $R^1$ | $R^2$ | $R^3$ | $R^6$ | Starting substance | Yield (%) | M.p. (° C.) |
|---|---|---|---|---|---|---|---|
| 43 | 2-CH$_3$ | H | H | CH$_3$ | 2-(2-methylphenoxy)ethyl bromide[a] | 87 base | 177–178 HBr salt |
| 44 | 2-CH$_3$ | 3-CH$_3$ | CH$_3$ | CH$_3$ | [2-(2,3-dimethylphenoxy)-1-methylethyl]-4-toluenesulfonate (Example 38) | 70 fumarate | 146–149 fumarate |
| 45 | 2-CH$_3$ | 5-CH$_3$ | CH$_3$ | CH$_3$ | [2-(2,5-dimethylphenoxy)-1-methylethyl]-4-toluenesulfonate (Example 37) | 65 HCl salt | 100–102 HCl salt |
| 46[b] | 2-CH$_3$ | 6-CH$_3$ | (R)-CH$_3$ | CH$_3$ | (S)-[2-(2,6-dimethylphenoxy)-1-methylethyl]-4-toluenesulfonate (Example 40) | 88 base | 187–188* HBr salt |
| 47[b] | 2-CH$_3$ | 6-CH$_3$ | (S)-CH$_3$ | CH$_3$ | (R)-[2-(2,6-dimethylphenoxy)-1-methylethyl]-4-toluenesulfonate (Example 39) | 84 base | 188–189** HBr salt |
| 48 | 2-CH$_3$ | H | CH$_3$ | CH$_3$ | [2-(2-methylphenoxy)-1-methylethyl]-4-toluenesulfonate (Example 41) | 89 base | 106–107 HBr salt |
| 49 | 2-CH(CH$_3$)$_2$ | H | CH$_3$ | CH$_3$ | [2-(2-isopropylphenoxy)-1-methylethyl]-4-toluenesulfonate (Example 42) | 96 base | 81–83 HCl salt |

[a]Beilstein 6, 352; [b]DE 2,524,363
*46. $\alpha_D^{20}$ = −5.0° (c = 1, methanol); **47. $\alpha_D^{20}$ = +4.0° (c = 1, methanol).

Preparation of Compounds of Formula (III)

EXAMPLE 50

N-[2-(2,3-Dimethylphenoxy)-1-methylethyl]-N-methyl-2-(4-methanesulfonamido-phenyl)-acetamide To a solution containing 0.80 g (3.5 mmol) of 4-methanesulfonamido-phenylacetic acid (Example 32) in 6H, N—CH$_3$ and S—CH$_3$); 3.72–4.05 (m, 4H, O—CH$_2$—CH and CO—CH$_2$—Ar); 4.45 (m) and 5.15 (m) (total 1H, CH$_2$—CH—N); 6.70 (dd, 1H), 6.83 (t, 1H) and 7.05 (dd, 1H) (2,3-dimethylphenoxy group); 7.10–7.22 (m, 4H, 4-methansulfonamidophenyl group); 7.50 (s, 1H, Ar—NH—S).

EXAMPLE 51

N-[2-(2,5-Dimethylphenoxy)-1-methylethyl]-N-methyl-2-(4-methanesulfonamido-phenyl)-acetamide To a solution containing 0.52 g (2.7 mmol) of N-methyl-2-(2,5-dimethylphenoxy)-1-methylethylamine (Example 45) in 15 ml of tetrahydrofuran 0.63 g (2.7 mmol) of 4-methanesulfonamido-phenylacetic acid (Example 32) and 0.63 g (3.05 mmol) of dicyclohexylcarbodiimide are added and the reaction mixture is stirred at room temperature for 16 hours. After filtration of the mixture, the filtrate is evaporated under reduced pressure and the pale yellowish resin of about 4.5 g obtained is purified by column chromatography by using a mixture of ethyl acetate and hexane as eluent. Thus, 0.76 g (70%) of the title compound is obtained as an amorphous material.

$^1$HMR (CDCl$_3$): 1.18–1.36 (m, 3H, C—CH$_3$); 2.10–2.18 (m, 3H) and 2.25–2.35 (m, 3H) (Ar—CH$_3$); 2.84–3.04 (m, 6H, N—CH$_3$ and S—CH$_3$); 3.66 (s) and 3.80 (s) (total 2H, CO—CH$_2$—Ar); 3.85–4.05 (m, 2H, O—CH$_2$—CH); 4.44 (m) and 5.10 (m) (total 1H, CH$_2$—CH—N); 6.56–6.62 (m, 1H), 6.62–6.74 (m, 1H) and 6.96–7.04 (m, 1H) (2,5-dimethylphenoxy group); 7.05–7.20 (m, 4H, p-methansulfonamido-phenyl group); 7.50–7.80 (m, 1H, Ar—NH—S).

EXAMPLE 52

N-[2-(2-Chlorophenoxy)-1-metbylethyl]-N-methyl-2-(4-methanesulfonamido-phenyl)acetamide The title compound is prepared as described in Example 50, except that N-methyl-2-(2-chlorophenoxy)-1-methylethylamine (FR. M. 5,912) is used as starting material to give a yield of 68% in the form of an amorphous material.

$^1$HMR (CDCl$_3$): 1.25–1.40 (m, 3H, C—CH$_3$); 2.90–3.00 (m) and 3.12 (s) (total 6H, N—CH$_3$ and S—CH$_3$); 3.70 (s) and 3.85–4.20 (m, total 4H, O—CH$_2$—CH and CO—CH$_2$—Ar); 4.52 (m) and 5.08 (m) (total 1H, CH$_2$—CH—N); 6.85–7.40 (m, 8H, Ar); 7.45–7.60 (m, 1H, Ar—NH—S).

What is claimed is:

1. Compounds of formula (I)

(I)

wherein $R^1$ and $R^2$, independently from each other, mean hydrogen, halogen or $C_{1-4}$ alkyl group;

$R^3$, $R^4$ and $R^5$, independently from each other, stand for hydrogen or $C_{1-4}$ alkyl group;

$R^6$ represents hydrogen, $C_{1-4}$ alkyl or benzyl group;

$R^7$ means nitro group or amino group optionally mono-substituted by $C_{1-4}$ alkyl, benzoyl, $C_{1-4}$ alkylcarbonyl, $C_{1-4}$ alkylsulfonyl, $C_{1-4}$ alkylcarbamoyl or $C_{1-4}$ alkylthiocarbamoyl group;

both n and m are 0 or 1, with the proviso that $R^2$ is different from hydrogen, when $R^1$ is hydrogen, as well as stereoisomers or mixtures of stereoisomers thereof, acid addition salts thereof and hydrates, prodrugs and metabolites of all these compounds.

2. A compound as claimed in claim 1, selected from the group consisting of

N-[4-[2-[N-methyl-N-[2-(2,6-dimethylphenoxy)-1-methylethyl]-amino]ethyl]phenyl]methanesulfonamide, (S)-N-[4-[2-[N-methyl-N-[2-(2,6-dimethylphenoxy)-1-methylethyl]amino]ethyl]phenyl]methanesulfonamide, (R)-N-[4-[2-(N-methyl-N-[2-(2,6-dimethylphenoxy)-1-methylethyl]amino]ethyl]phenyl]methanesulfonamide, N-[4-[2-[N-methyl-N-[2-(2-methylphenoxy)ethyl]amino]ethyl]-phenyl]methanesulfonamide, N-[4-[2-[N-methyl-N-[2-(2,6-dimethylphenoxy)-1-methylethyl]-amino]ethyl]phenyl]acetamide, N-[4-[2-[N-[2-(2,6-dimethylphenoxy)-1-methylethyl]-amino]ethyl]phenyl]methanesulfonamide, 1-Methyl-3-[4-[2-[N-methyl-N-[2-(2,6-dimethylphenoxy)-1-methylethyl]amino]ethyl]phenyl]thiourea, 2-[4-Aminophenyl]-N-methyl-N-[2-(2,6-dimethylphenoxy)-1-methylethyl]ethylamine and the acid-addition salts of these compounds.

3. A pharmaceutical composition, which comprises as active ingredient a compound of formula (1), wherein $R^1$, $R^2$, $R^3$, $R^4$, $R^5$, $R^6$, $R^7$, n and m are as defined in claim 1, or a therapeutically acceptable salt or hydrate thereof in admixture with solvents, diluting agents, carriers and additives commonly used in the preparation of medicaments.

4. A method of treating diseases in mammals accompanied by arrhythmia, which comprises administering to a mammal in need of such treatment an antiarrhythmic amount of a compound of claim 1.

* * * * *